United States Patent
Cordero et al.

(10) Patent No.: US 6,298,255 B1
(45) Date of Patent: Oct. 2, 2001

(54) SMART ELECTROPHYSIOLOGICAL SENSOR SYSTEM WITH AUTOMATIC AUTHENTICATION AND VALIDATION AND AN INTERFACE FOR A SMART ELECTROPHYSIOLOGICAL SENSOR SYSTEM

(75) Inventors: Rafael M. Cordero, Tewksbury; Philip H. Devlin, Brookline; Nassib G. Chamoun, Needham; John R. Shambroom, Arlington; Edwin B. Merrick, Stow; Joao Melo, Southborough, all of MA (US)

(73) Assignee: Aspect Medical Systems, Inc., Newton, MA (US)

( * ) Notice: Subject to any disclaimer, the term of this patent is extended or adjusted under 35 U.S.C. 154(b) by 0 days.

(21) Appl. No.: 09/328,945

(22) Filed: Jun. 9, 1999

(51) Int. Cl.⁷ .................................................. A61B 5/0408
(52) U.S. Cl. ............................................................ 600/372
(58) Field of Search .................................... 600/300, 301, 600/331, 332, 372, 509; 606/1; 128/897, 920; 607/2, 59, 62, 115, 134

(56) References Cited

U.S. PATENT DOCUMENTS

| | | |
|---|---|---|
| 4,580,557 | 4/1986 | Hertzmann . |
| 4,684,245 | 8/1987 | Goldring . |
| 4,868,476 | 9/1989 | Respaut . |
| 4,942,877 | 7/1990 | Sakai et al. . |
| 5,058,588 | 10/1991 | Kaestle . |
| 5,125,405 | 6/1992 | Schmid . |
| 5,198,955 | 3/1993 | Willner . |
| 5,305,746 | 4/1994 | Fendrock . |
| 5,357,953 | 10/1994 | Merrick et al. . |
| 5,441,528 * | 8/1995 | Chang et al. ............................ 607/69 |
| 5,458,117 | 10/1995 | Chamoun et al. . |
| 5,660,177 | 8/1997 | Faupel et al. . |
| 5,660,567 | 8/1997 | Nierlich et al. . |
| 5,813,404 | 9/1998 | Devlin et al. . |
| 5,830,129 * | 11/1999 | Baer et al. ............................ 600/300 |
| 5,876,351 * | 3/1999 | Rohde ................................... 600/523 |

FOREIGN PATENT DOCUMENTS

| | | |
|---|---|---|
| 280450 | 8/1988 | (EP) . |
| WO 9221163 | 11/1992 | (WO) . |
| WO 9306776 | 4/1993 | (WO) . |
| WO 9401039 | 1/1994 | (WO) . |
| WO 9729678 | 8/1997 | (WO) . |

OTHER PUBLICATIONS

Standard 60601, Common Aspects of Electrical Equipment Used in Medical Practices, Ed. 2.0, The International Electrotechnical Commission, Geneva, Switzerland, 1988.

Rivest, R.L. et al., "A Method for Obtaining Digital Signatures and Public–Key Cryptosystems," Communications of the ACM, vol. 21, pp. 120–126, Feb. 1978.

"Digital Signature Standard," National Institute of Standards and Technology, FIPS Publication 186,1993.

ElGamal, T., A Public Key Cryptosystem and a Signature Scheme Based on Discrete Logarithms, Advances in Cryptology—Proceedings of CRYPTO '84, Springer Verlag Lecture Notes in Computer Science 196, pp. 10–18, 1985.

Schnorr, C.P., "Efficient Signature Generation by Smart Cards," Journal of Cryptology, vol. 4, pp. 161–174, 1991.

* cited by examiner

Primary Examiner—William E. Kamm
(74) Attorney, Agent, or Firm—Hale and Dorr LLP

(57) ABSTRACT

A sensor system which includes a biopotential signal monitor, a smart sensor and the accompanying hardware and software interface which authenticates the source and validity of the smart sensor and also verifies that the smart sensor meets various criteria for use.

53 Claims, 19 Drawing Sheets

SMART ELECTROPHYSIOLOGICAL SENSOR SYSTEM WITH AUTOMATIC AUTHENTICATION AND VALIDATION AND AN INTERFACE FOR A SMART ELECTROPHYSIOLOGICAL SENSOR SYSTEM

BACKGROUND OF THE INVENTION

This invention relates to electrophysiological sensors and more particularly to an electrophysiological sensor system which allows the automatic authentication and configuration of the sensor.

When using biomedical sensors to acquire electrophysiological signals for recording and analysis, it is desirable to make certain information concerning the sensor available to the recording and analysis device (monitor). Useful information includes the configuration of electrodes on an electrode sensor, the date of manufacture of the sensor, the identity of the manufacturer and the manufacturer's lot number. A monitor can utilize this information to determine the manner in which to process the acquired data, or even whether to allow the use of the sensor at all (e.g., in the case of an expired sensor).

Such data is entered into the monitor manually by the user, by means of a keyboard, by using a bar code reader to enter data printed on a tag supplied with the sensor, or by various information programs. A simpler method to enter the data is to store the desired information in a memory device of some kind integrated into the sensor itself. The monitor then reads the information automatically, saving the user time and trouble. Various information programs running on the monitor use this information to determine not only the characteristics of the sensor for configuration purposes, but also to verify the viability of a limited life-time sensor, to verify its authenticity and to record various data acquired from the sensor.

The integration of memory devices with medical sensors is well known in the art. In U.S. Pat. No. 5,813,404, Devlin, et al. describe a biopotential electrode connector system in which the configuration of the electrode array is stored in a set of logic lines (jumpers) in the connector of an electrode interface cable. The arrangement described provides for only 8 unique codes, and thus the amount of information which may be stored is severely limited. Also in this invention, the connection of a sensor to the monitor is automatically detected. The monitor incorporates a pulse generator, the pulses of which are used to sense the status of the jumpers (jumpered or open). The determined code is subsequently used to configure the monitor for the particular electrode configuration. This method of automatic sensor detection is suitable for use with passive, hardwired jumpers, but requires a separate pulse generator circuit.

In U.S. Pat. No. 4,580,557, Hertzmann describes the use of coding resistors in the connector of a surgical laser system peripheral output device which serve to identify the particular peripheral device in use. The amount of information that may be stored is again very limited.

In U.S. Pat. No. 5,660,567, Nierlich et aL describe the use of a coding resistor incorporated into a separate module that plugs into the connector of an oximeter probe. Nierlich et aL use the resistor as a mans to code the center wavelength of the red probe emitter. The use of a resistor as a storage device severely limits the amount of information that may be stored.

In U.S. Pat. No. 5,058,558, Kaestle states that the place of application (finger, ear, nose, foot, toe, etc.) of an oximeter has an effect of the accuracy of the measurement. He therefore describes a system for coding the type of sensor (finger sensor, ear sensor, etc.) as a surrogate for the place of application. The code is preferably stored in a coding resistor incorporated in the sensor, which severely limits the amount of information that can be stored. An alternate embodiment would comprise a ROM (read-only memory) or customized integrated circuit, also located in the sensor. While providing more data storage capacity, this embodiment does not provide security for the stored information, nor does it provide the capability for the monitor to store data on the sensor. In addition, the alternate embodiment requires a custom semiconductor device rather than an off-the-shelf device.

In U.S. Pat. No. 4,942,877, Sakai and Hamaguri describe the use of a memory device in or on an oximeter probe; the exact location is not specified. In this probe, the memory device is used to store calibration data relating to the light emitting diode (LED) emitters. An EPROM (electrically programmable, read-only memory) or EEPROM (electrically erasable, programmable, read-only memory) memory device is used. This embodiment does not provide security for the stored information.

In U.S. Pat. No. 4,684,245, Goldring describes the use of a memory chip with a fiberoptic oximeter catheter to store calibration signals. The memory chip is not incorporated into the disposable catheter, but rather into an interface module which can be disconnected from the monitor for transport purposes, so that the calibration data is transported along with the catheter and may be reconnected to a different monitor without necessitating a recalibration.

In U.S. Pat. No. 5,357,953, Merrick, et al describe a similar system for storing calibration data in a separate memory device associated with an invasive optical blood gas analyzer sensor. The blood gas analyzer contains a processor and each disposable blood gas sensor is associated with a self-contained, non-integral non-volatile memory device preferably described as an EEPROM, and alternately as a RAM (random access memory), ROM (read-only memory) or EPROM. The memory device is used to store calibration data specific to the sensor with which it is associated, so that the sensor may be transferred to other blood gas analyzers without recalibration.

In U.S. Pat. No. 4,868,475, Respaut describes the use of a memory device in the transducer system of a scanning mechanical ultrasonic transducer system. The memory device is positioned in the plug of the transducer system connecting the transducer to the associated monitor. The memory device is preferably an EEPROM, but alternately an EPROM or PROM (programmable, read-only memory) and is used to store nonlinearity error information or other information concerning errors in the positioning or scan control for the particular transducer or other calibration information.

In U.S. Pat. No. 5,660,177, Faupel et aL describe an electrode for measuring DC biopotentials that incorporates an addressable chip mounted in either the connector or the cable. This chip, which may be an EEPROM, is designed to be addressed by the processor at a known address. At the start of monitoring, the monitor attempts to interrogate the chip by reading from the preestablished memory location that corresponds to the addressable chip. If the monitor is able to read the memory location corresponding to this address, it proceeds with the measurement program; if it can not read this location, it does not proceed with the measurement program. Faupel further discloses that the monitor may prevent reuse of the electrode by erasing the memory device. Faupel does not specify what information is stored in this memory device or whether the measurement program makes further use of it beyond verifying the presence of an electrode.

While all the devices described above are medical sensors that incorporate some form of memory, they are limited to simply storing calibration and/or configuration data. In contrast, an ideal electrophysiological signal sensor would have the capability to store specific data concerning the sensor itself, such as lot codes, the date of expiration and the sensor serial number, in addition to configuration data It would also encode the identity of the manufacturer and distributor and would encrypt the stored data in order to both protect its integrity and prevent the use of unauthorized substantially equivalent devices. None of the devices described in the patents cited above encrypt the stored data, identify the manufacturer or distributor, use a secure memory device or protect the associated monitor from use with an unauthorized sensor.

The ideal sensor, then, is one that incorporates means for the authentication of its source and the validation of the data stored in its memory. Such a "Smart Sensor" will be part of a sensor authentication and validation system, of which the monitor to which it is connected and which processes the acquired electrophysiological signals is an integral part. The software running in the associated monitor would not only read the data stored on the smart sensor, but also decrypt the data and use it to perform a series of authentications and validations which verify the source of the smart sensor and its physical integrity, while logging its characteristics and various data concerning the conditions of its use. The physical design of the smart sensor, the data stored on it and the accompanying encryption techniques would protect the smart sensor from counterfeiting and provide improved monitoring performance. In addition, such a smart sensor system allows selective functionality to be obtained from a single monitoring system, depending on various configuration codes stored on the smart sensor. Additional functionality may be added after the date of manufacture of the monitor by simply storing different configuration codes on the smart sensor and updating the monitor software.

Another challenge in designing a patient connected sensor which incorporates active electronics in close proximity to a patient is to prevent the application of excess electric current to the patient in both normal and fault conditions

SUMMARY OF THE INVENTION

The present invention provides a sensor system which includes a biopotential signal monitor, a smart sensor and the accompanying hardware and software interface which authenticates the source and validity of the smart sensor and also verifies that the smart sensor meets various criteria for use.

The smart sensor integrates an array of electrodes with a secure memory device. The array of electrodes, when placed on a body surface, is used to acquire biopotential signals from a subject. A plurality of electrodes making up the array are integrated onto the surface of a flexible substrate. A plurality of electrical conductors are printed on the surface of the array and provide an electrical conduction path from the electrodes to a terminal tab. The terminal tab is attached to a plastic molded interface platform which provides mechanical stiffness allowing the conductors on the tab to be inserted into the mating receptacle of a biopotential monitor. An off-the-shelf smart card semiconductor memory module containing ROM, PROM and EEPROM is also mounted on the interface platform. The smart card memory module contains in ROM a code unique to the purchaser of the memory module which can be used to validate the source of the smart sensor. Such source validation is not possible with standard ROM, PROM or EEPROM memory devices. The electrical contact pads on the memory module make contact with complementary contact points inside the mating receptacle when the interface platform and mating receptacle are joined. The use of off-the-shelf secure smart card modules has distinct advantages for the smart sensor, including the security provided by the module and the advantages to the construction of the smart sensor provided by the smart card module's physical configuration.

The smart sensor mating receptacle interfaces mechanically with the interface platform as a tab connection. This includes mechanical keying for proper orientation, a locking feature, contact areas for the smart card memory and the sensor traces, and prevention of ingress of liquids. The ingress of liquids into the receptacle is not desirable as it can result in an electrical hazard to the patient, as well as cause poor electrical performance of the instrumentation due to shorting between signal leads. Accordingly, a goal of this invention is a means to provide a reasonable seal to the ingress of liquids during both use and idle modes. For this purpose, an elastomer door is present at the entrance of the connector. In addition, an elastomer wiping surface is present that will remove any excess water from a mating part as it is inserted into the receptacle.

The system detects the presence of the sensor by detecting the electric current required to power the smart card memory module upon connection to the mating receptacle. This current can be detected in either the power conductor or the return conductor. When a current in excess of a threshold is detected, the monitor is signaled that a smart sensor has been connected to the mating receptacle. The monitor software then initiates a smart sensor authentication and validation sequence.

The presence of an active electronic device (the smart card memory module) on the smart sensor in close proximity to the patient poses unique design issues relating to maintaining patient safety in both normal and single fault conditions (so called "auxiliary current" in the IEC 60601 Standard (Standard 60601, Common Aspects of Electrical Equipment Used in Medical Practice, Ed. 2.0, The International Electrotechnical Commission, Geneva, Switzerland, 1988). Such a condition might result from a failure of the instrumentation amplifiers connected to the patient electrode leads, as well as a short between the conductors of the smart sensor, the mating receptacle or the intermediary cable connecting the smart sensor and the monitor. A failure might also result from the short-circuiting of the conductive leads on either the smart sensor or in the mating receptacle due to the ingress of fluid into these areas. Such a failure condition might result in the supply current of the memory module or instrumentation amplifiers being applied to the patient leads, with the resulting application of unacceptable levels of current being applied to the patient.

The smart sensor interface circuit prevents auxiliary current from being conducted through the patient in the event of a single fault in several ways. First, the system monitors the current in the patient ground, and turns power off to the smart sensor if excess current is detected. Second, an electrically grounded "guard" path is interposed between the smart sensor circuits and patient connected circuits both on the sensor and in the reusable mating receptacle. This guard path acts as a current sink in the event of a fault condition, harmlessly conducting the excess current away from the patient. The guard thus prevents contaminants on the surface from bridging between the memory module conductors and the patient conductors.

Various data concerning the origin and manufacture of the smart sensor are stored in the memory module. This data includes, but is not limited to, a key code, a manufacturer code, an original equipment manufacturer (OEM) code, a product shelf life code, a sensor type code, the sensor lot number and serial number and the usage count. All or a part of the data are stored in encrypted form A digital signature is also stored on the smart sensor. The monitor uses this stored data to authenticate the attached smart sensor.

When the smart sensor interface circuit detects the connection of the monitor, the monitor software reads the data from the smart sensor. The monitor software first verifies that the manufacturer code indicates that the smart sensor was manufactured by an authorized source.

Since it is anticipated that there will be multiple distributors of smart sensors and multiple licensed manufacturers of monitors, the monitor software will also check the OEM code against a look-up table to determine whether the smart sensor is allowed to be used with the specific monitor. If the data cannot be read from the smart sensor, or if the smart sensor did not originate at an authorized manufacturer, or if the OEM code does not correspond with one that is allowed to be used with the particular monitor, the monitor software refuses to proceed with monitoring. If all of the foregoing conditions are met, the monitor software next verifies the digital signature using one of several decryption keys specified by the key code and decrypts the smart sensor data If the digital signature cannot be verified or the data cannot be decrypted, the monitor software refuses to proceed with monitoring.

The monitor next logs the smart sensor identification data into its non-volatile memory. The monitor uses the smart sensor serial number to maintain a usage counter for each individual smart sensor that it authenticates. The usage counter records the number of times that a specific smart sensor has been authenticated. After successfully authenticating a smart sensor a preset maximum number of times, the monitor will refuse further authentications of that particular smart sensor. This allows reuse of the smart sensor to be limited for quality and infection control purposes, while still allowing for legitimate disconnection and reconnection and allows the monitor to warn the user if the connected smart sensor has already been used. This feature is important with devices with limited lifetimes or whose performance degrades with every use. The usage counter also provides a defense against multiple unauthorized smart sensors manufactured with the same serial number. A mirror usage counter is maintained in the smart sensor memory. The smart sensor and monitor usage counters are synchronized to the minimum of uses remaining between the two during the authentication process. This ensures that the current usage count reflects the sum of all prior usage independent of the monitor to which the smart sensor was connected.

In addition to the usage data, the monitor records in the log the time and date of use of each smart sensor. This data may be used by the manufacturer for customer service, quality control and product improvement purposes.

The monitor software next uses the sensor type code which indicates which of several possible data processing algorithms is appropriate for use with the specific smart sensor type. The monitor software next verifies that the smart sensor lifetime has not yet expired, notifying the user if the smart sensor is beyond its recommended shelf life. The monitor then proceeds with monitoring.

In an alternative embodiment, the monitor may use the smart sensor's memory module as a data archive, storing patient and performance data. The smart sensor may then be returned to the manufacturer, who may access the data stored in the memory for purposes of product improvement. Alternatively, the information may be transferred to a computer in the field.

In another alternative embodiment, the smart card module may be of the type containing an integral microprocessor. This modification would then provide the smart sensor with additional security by enabling it to respond to a "challenge" by the monitor. As part of the authentication process, the monitor may challenge the smart sensor by transmitting a random number to it. The smart sensor then encrypts the number and transmits it back to the monitor. The monitor subsequently decrypts the received number and compares it to the transmitted number; if the two match, the smart sensor is encrypting data using the correct algorithm and security key, rather than simply transmitting a stored data string.

DETAILED DESCRIPTION OF PREFERRED EMBODIMENTS

The mechanical aspects of the sensor system of the present invention are based on a plastic molded interface and mounting platform that serves as an assembly base for the various components of the system. The interface platform ensures that the system components are maintained in the correct relative alignment and provides sufficient mechanical stiffness to enable the terminal tab/smart sensor/interface platform assembly to be removably inserted into a mating receptacle. The union of the smart sensor 2 and the mating receptacle 6 achieves an electrical connection between the components of the smart sensor 2 and the associated monitor. The monitor may then perform analysis and/or recording of the acquired biopotentials.

Figure 1:
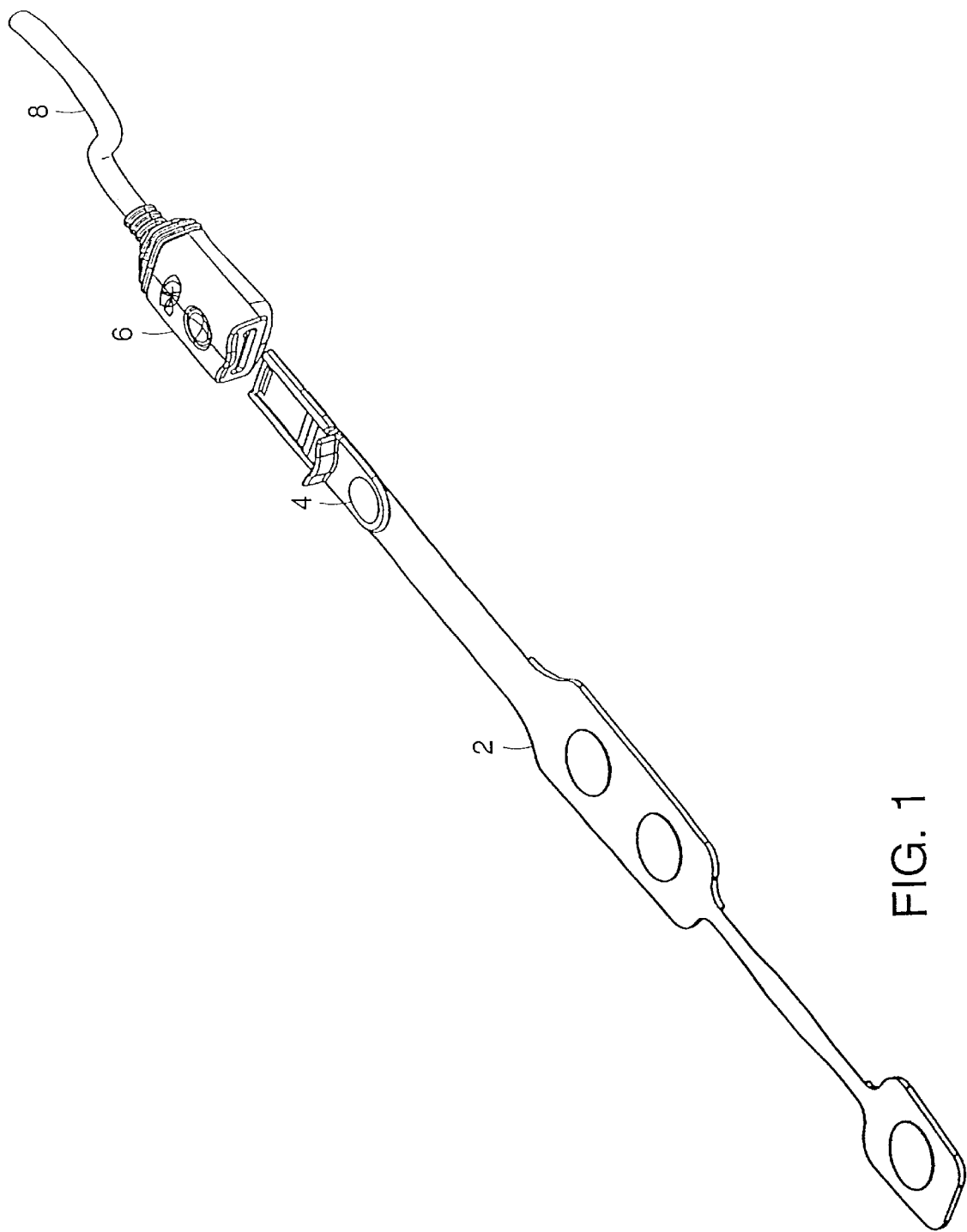
FIG. 1 is a perspective view of the smart sensor of the present invention and mating receptacle.

Referring to FIG. 1, the perspective view shows the entire smart sensor assembly. This includes the smart sensor 2 with an integral plastic molded interface and mounting platform 4, and the mating receptacle 6. The plastic molded interface platform 4 serves as a structure to which a memory module and terminal tab of the sensor substrate are mounted and also holds these components in proper alignment for insertion into the mating receptacle 6. The mating receptacle 6 is connected to a monitor (not shown) by a cable 8. The mating receptacle 6 is sealed to prevent the ingress of liquids and provides a wiping action to prevent the insertion of a wet plastic sensor tab.

Figure 2:
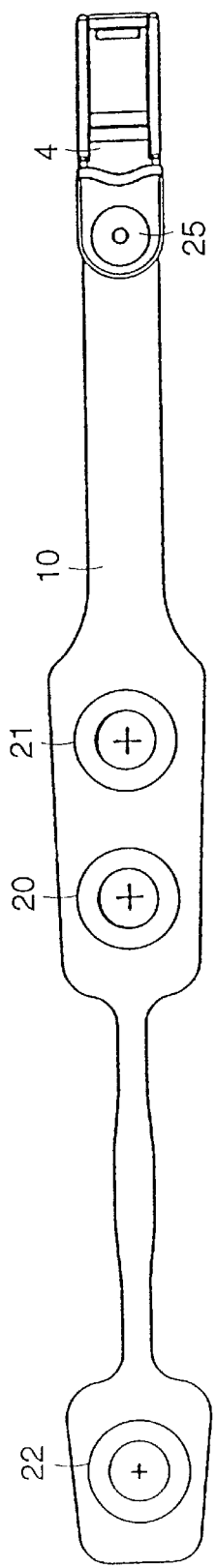
FIG. 2 is a top plan view of the smart sensor shown in FIG. 1.

FIG. 2 shows the flexible substrate 10 that serves as a substrate for the electrodes 20, 21, 22 of the electrode array and the set of printed conductors which electrically connect the electrodes to the mating receptacle 6. The positions of the array of three electrodes 20, 21, 22 are delineated by the circle locations. The plastic molded interface platform 4 serves as the connecting platform. A thumb grip 25 facilitates insertion of the molded interface platform 4 into the mating receptacle 6.

Figure 3:
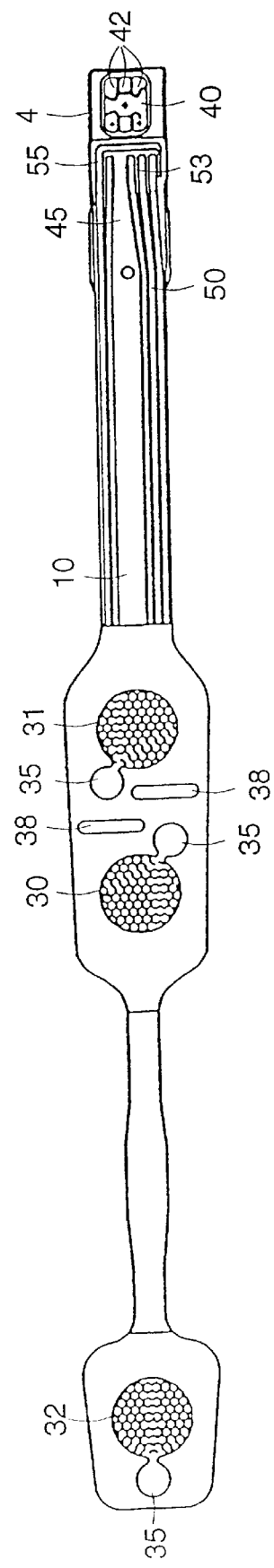
FIG. 3 is a plan view of the underside of the smart sensor shown in FIG. 1.

FIG. 3 shows the three electrodes 20, 21, 22 from the bottom side. These electrodes contain conductive gel, a gel-retaining sponge 30, 31, 32 and self-prepping times of the type described in U.S. Pat. No. 5,305,746, the teachings of which are incorporated herein by reference. These electrodes incorporate gel blowout compartments 35 and salt-bridge barriers 38; these features provide a location for excess gel to expand into and prevent excess gel from short-circuiting adjacent electrodes or lifting the sensor off the skin. The plastic molded interface platform 4 serves as a mounting and interfacing platform for the smart card memory module 40 and the proximal end of the flexible circuit substrate 10, referred to as the terminal tab 45. Adhesively mounting the terminal tab and the memory module 40 on the interface platform holds these components in precise alignment to each other, so that the printed conductors 50 on the terminal tab 45 and the contact pads 42 of the memory module 40 are positioned to make the proper electrical contact upon insertion of the interface platform 4 into the mating receptacle 6. The memory module 40 and the terminal tab 45 are mounted on the interface platform 4 so that they are physically and electrically separate. This prevents current from the electrical power supply of the memory module 40 from coming into contact with the patient-connected printed conductors 50 on the terminal tab 45, acting to assure patient safety. A ground guard trace 55 that encircles the exposed contacts 53 of the printed conductors 50 serves as a further means of patient protection. The ground guard trace 55 acts as a current sink thus preventing an electrical path between the memory module 40 and the printed conductors 50, as might occur in the event of ingress of liquid into the mating receptacle 6.

Figure 4A:
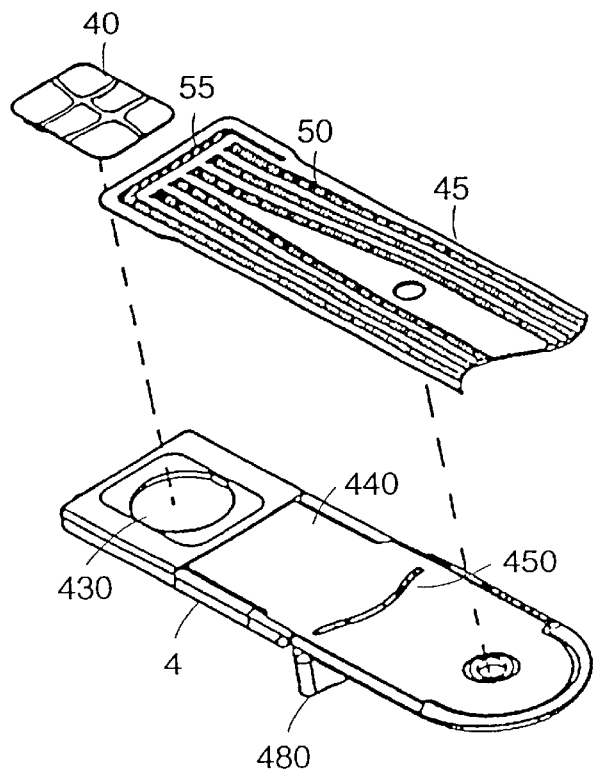
FIG. 4(a) is a perspective exploded view of the plastic molded interface platform, showing the mounting of the terminal tab and smart card memory module, and ground guard.

The smart sensor plastic molded interface platform assembly is shown in FIG. 4(a). The precisely formed plastic molded interface platform 4 is preferably molded of acrylonitrile butadiene styrene (ABS) plastic. The memory module 40 and the terminal tab 45 of the flexible plastic substrate are permanently attached to the interface platform 4 with a drop of liquid adhesive or a hot melt adhesive laminate. The memory module 40 has a protrusion (not shown) on the side opposite from the electrical contact pads 42. The protrusion fits into an alignment cavity 430 on the interface platform 4. This cavity 430 serves as a mounting point for the memory module 40, ensuring proper positioning during manufacturing. If liquid adhesive is used, a drop is placed in the alignment cavity 430 and the memory module 40 is pressed into place, the adhesive attaching it firmly to the interface platform 4. If hot melt adhesive is used, the laminate is die cut with the memory module 40 and placed into the alignment cavity 430 outline for further fixing with heat. The flexible plastic substrate 10 is preferably constructed of polyester, on one side of which are printed conductors 50 using conductive ink, preferably silver (Ag). These printed conductors 50 make connection to the biopotential electrodes 20, 21, 22 of the plastic substrate 10. The terminal tab 45 is adhesively attached to the tab mounting point 440 of the interface platform 4 such that the side of the tab 45 bearing the printed conductors 50 is opposite the interface platform 4. The interface platform 4 incorporates a raised portion 450 that presses the printed conductors 50 against the contact points (not shown) inside the mating receptacle 6.

Figure 4B:
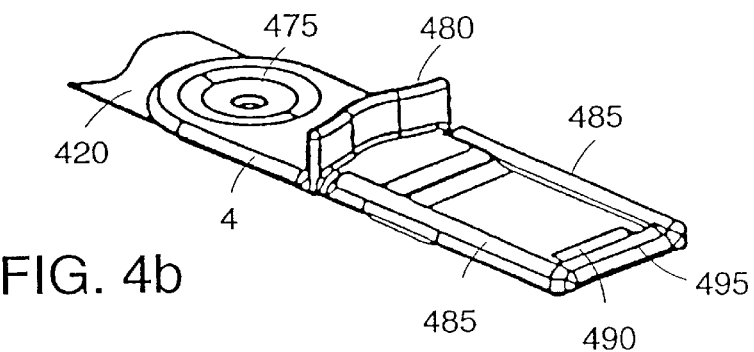
FIGS. 4(b) and 4(c) are perspective views of the assembled plastic molded interface platform, showing the mounting of the terminal tab and smart card memory device, and ground guard.

FIG. 4(b) shows the underside of the interface platform 4 with the attached memory module 40 and terminal tab 45. The smart card memory module 40 used in the invention incorporates integral electrical contact pads 42 on the module 40 itself. In the completed assembly, the surfaces of these pads 42 are aligned in the same orientation as the surfaces of the printed conductors 50 of the terminal tab 45. The integration of the memory module contact pads 42 on the memory module 40 has the important advantage of obviating the need for additional printed conductors on the flexible substrate to provide an electrical connection point for the memory module 40. A further advantage is that the electrical paths of the memory module connections are independent of those that connect the electrodes 20, 21, 22 to contact points in the mating receptacle 6. Separation of the memory module conduction path from that of the electrodes 20, 21, 22 isolates the patient from the electrical paths of the memory module 40, significantly enhancing patient safety. The relative placement of the memory module 40 and terminal tab 45 ensures that the printed conductor patient leads 50 will not momentarily come into contact with the memory module power supply and logic lines on the contact pads 42 during insertion and removal of the interface platform 4 from the mating receptacle 6. Physical separation of the analog signals carried on the printed conductor patient leads 50 and the digital signals on the memory module contact pads 42 enhances the noise immunity of the acquired signals. Further enhancing patient safety is an additional printed conductor 55 that serves as a grounded guard trace. The ground guard serves as a collection path for any stray electrical current that might result from a fault condition. It is placed between the contact pads 42 of the memory module 40 and the printed conductor patient leads 50 in such a manner that it provides a barrier to any current that might leak from the memory module contact pads 42.

Figure 4C:
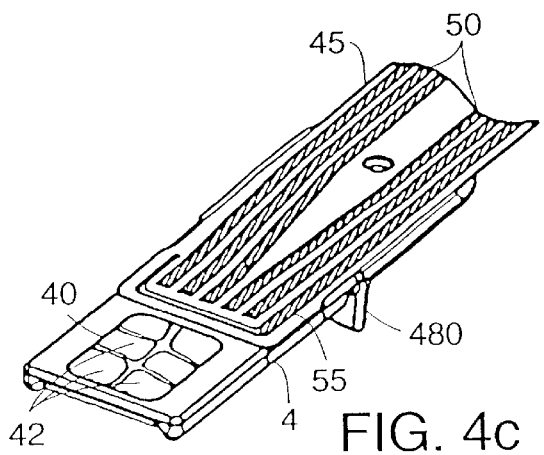

FIG. 4(*c*) shows the top of the interface platform 4. In this view, the side of the flexible substrate 10 opposite that bearing the printed conductors may be seen 420. To facilitate connection to the mating receptacle 6, the interface platform 4 incorporates a finger grip 475 which indicates where the interface platform 4 should be grasped. This helps to avoid finger contact with the exposed electrical contact surfaces on the underside of the interface platform 4, thus minimizing the risk of poor connection impedances due to residual epidermal oils. The interface platform 4 also incorporates a finger stop 480 which enables the user to exert the moderate degree of force necessary to firmly slide the interface platform into the mating receptacle. Integrated into the upper surface of the interface platform 4 is a pair of keyed alignment rails 485 along each side of the portion of the interface platform 4 that is inserted into the mating receptacle 6. The rails 485 ensure that the interface platform 4 can be inserted into the receptacle 6 in only one possible alignment. Also incorporated into the interface platform 4 are a retaining depression 490 and retaining restraint 495, which act together to retain the interface platform 4 within the mating receptacle 6.

Figure 5:
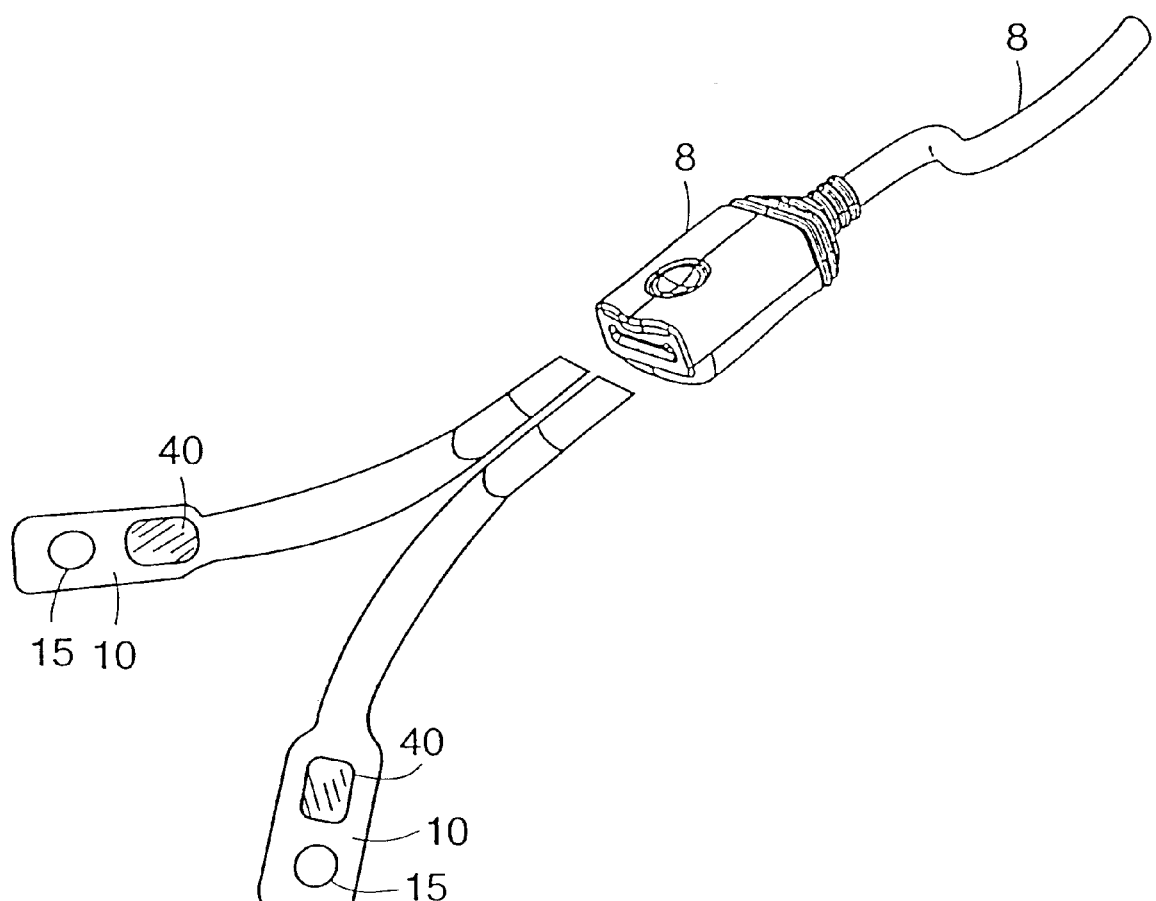
FIG. 5 is a perspective view of a smart sensor consisting of several smart electrodes.

It should be recognized that various alternative embodiments of the smart sensor may be constructed by substituting individual electrodes for some or all of the electrodes in the electrode array, by providing individual interface platforms for some or all of the electrodes, and by varying the location of the memory module. Individual electrodes substituted for some or all of the electrodes of the electrode array may have individual interface platforms, or may connect to a common interface platform, or a combination of the two. The memory module 40 may be placed on the electrode array substrate 10, on one of the individual electrodes 20, 21, 22, in a cable connecting the electrode array to a mating receptacle or monitor, or on or in an interface connector attached to the electrode array and connecting it to the mating receptacle. Alternatively, smart electrodes may be constructed by placing memory modules 40 on the substrate 10 carrying an individual electrode 15 as shown in FIG. 5, on each individual electrode 20, 21, 22, or on or in the interface connector of the smart electrode 18; a set of smart electrodes may then be connected by individual or common interface connectors to a mating receptacle 6 or monitor, creating a smart sensor. Such alternate embodiments are functionally equivalent to the preferred embodiment described above.

Figure 6A:
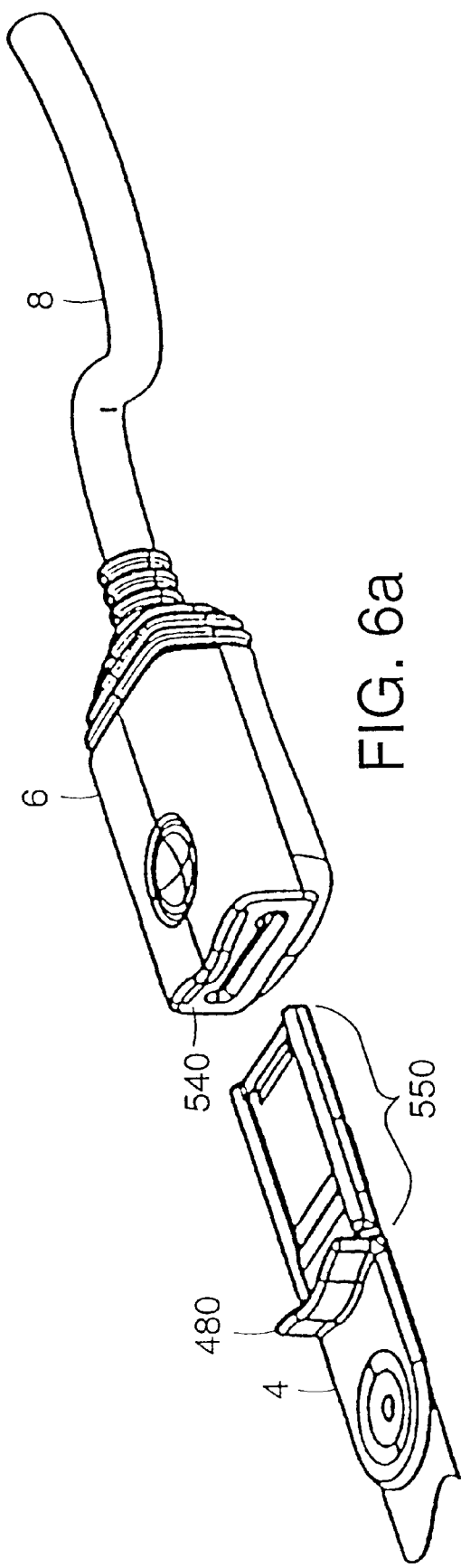
FIGS. 6(a) and 6(b) are perspective views of the plastic molded interface platform ready for insertion and fully inserted, respectively, into the mating receptacle.
Figure 6B:
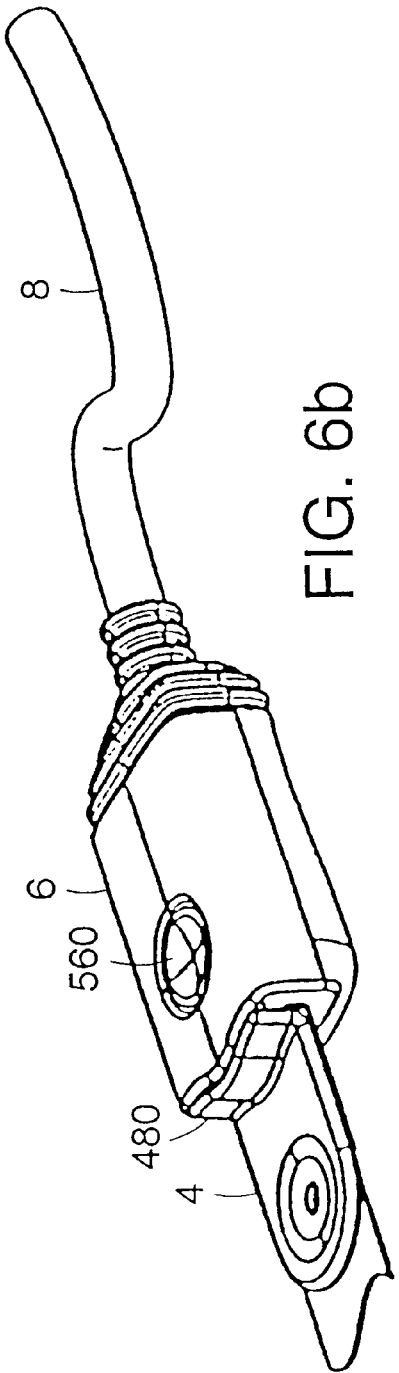

Electrical connection between both the printed conductors 50 connecting to the electrodes 20, 21, 22, the memory module 40 and the associated monitor (not shown) are achieved by means of a mating receptacle 6. The mating receptacle 6 contains numerous features specific to this invention and is an integral part of the smart sensor system of the present invention. A view of the interface platform 4 properly aligned for insertion into the mating receptacle 6 is shown in FIG. 6(*a*). The mating receptacle 6 may be attached to a biopotential signal monitor (not shown) containing a processor either directly or by means of an intermediary connecting cable 8. Referring now to FIG. 6(*b*), the interface platform 4 is inserted into the mating receptacle 6 until the finger stop 480 makes contact with the end face 540 of the mating connector 6. The portion 550 of the interface platform 4 that is inserted includes both the attached memory module 40 and the attached end of the terminal tab 45 bearing the printed conductors 50. Upon insertion, both the contact pads 42 on the memory module 40 and the printed conductors 50 on the terminal tab 45 make contact with electrical contact points (not shown) within the mating receptacle 6. This establishes an electrical connection between the printed conductors 50 of the electrode array 20, 21, 22 and the memory module 40 on one hand, and the internal conductors (not shown) of the connecting cable 8 of the signal monitor on the other.

Figure 7:
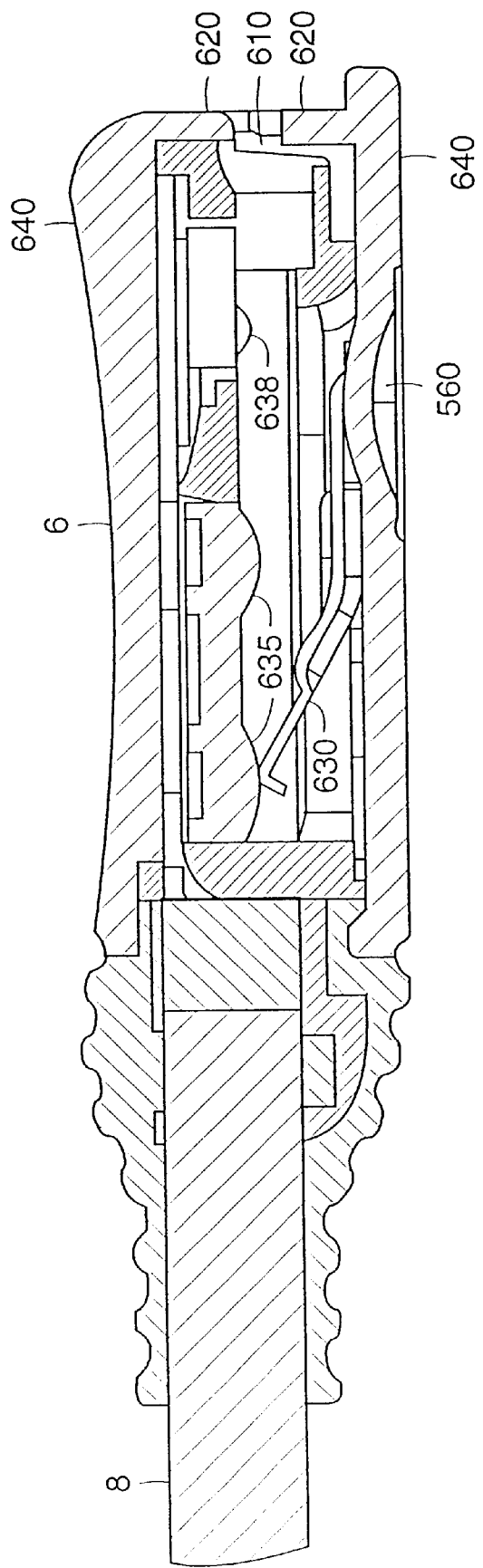
FIG. 7 is a side cross-sectional view mating receptacle, showing the electrical contact surfaces, the living hinge door and the wiping surfaces of the receptacle.

Referring now to FIG. 7, the mating receptacle 6 also incorporates a beryllium-copper retaining finger 630 that engages the retaining depression 490 when the interface platform 4 is fully inserted into the mating receptacle 6. When opposing forces are exerted in line with the smart sensor 2 and connecting cable 8 of the mating receptacle 6, the retaining finger 630 exerts a counter force against the retaining restraint 495, preventing the interface platform 4 from being inadvertently withdrawn from the receptacle 6. Pressing on the release button 560 lifts the retaining finger 630 out of the retaining depression 490 and clear of the retaining restraint 495, so that the interface platform 4 may be removed from the receptacle 6 and the smart sensor 2 disconnected when desired. In the case of the accidental application of an excessive pulling force on the smart sensor 2, the retaining finger 630 will yield and the interface platform 4 will then detach to prevent patient injury caused by a falling monitor.

Figure 8:
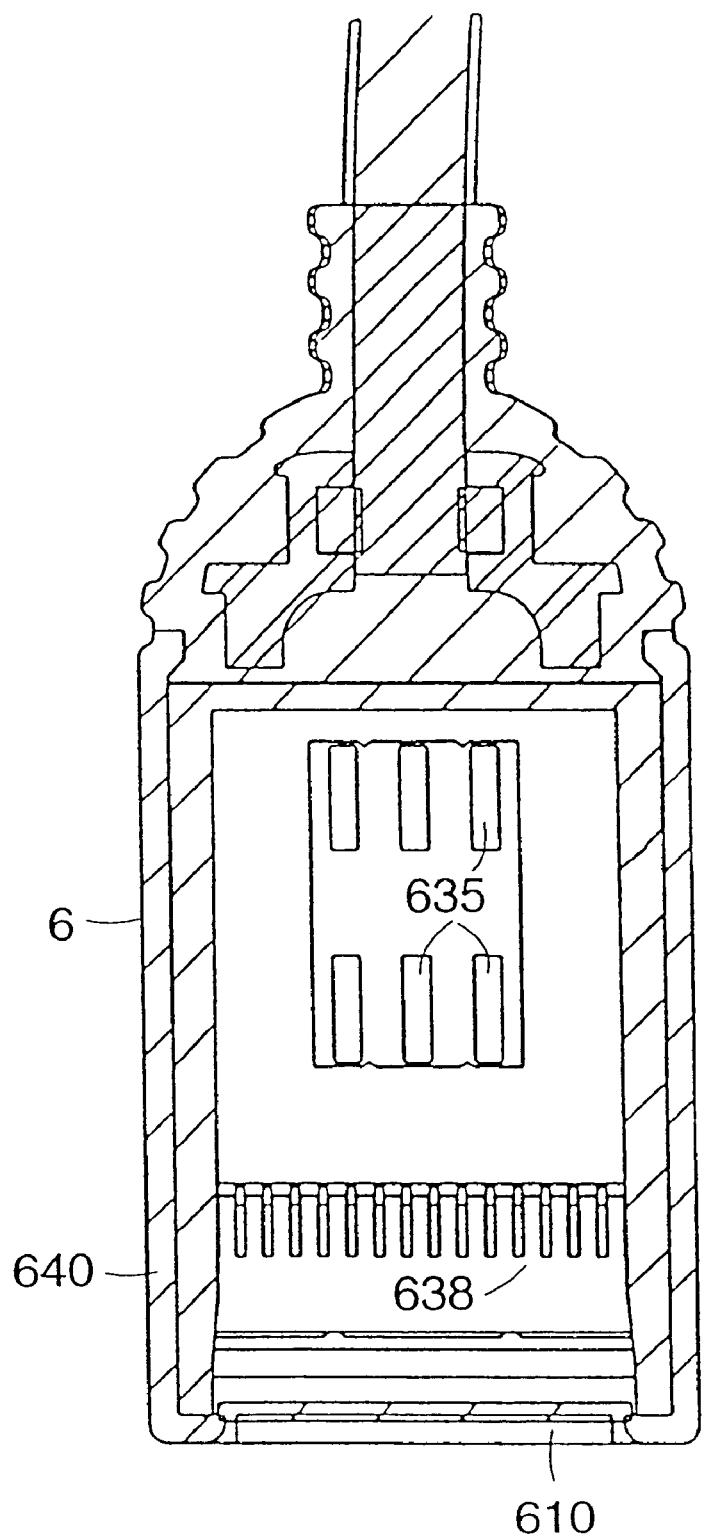
FIG. 8 is a cross-sectional view of the mating connector showing the electrical contact surfaces.
Figure 9:
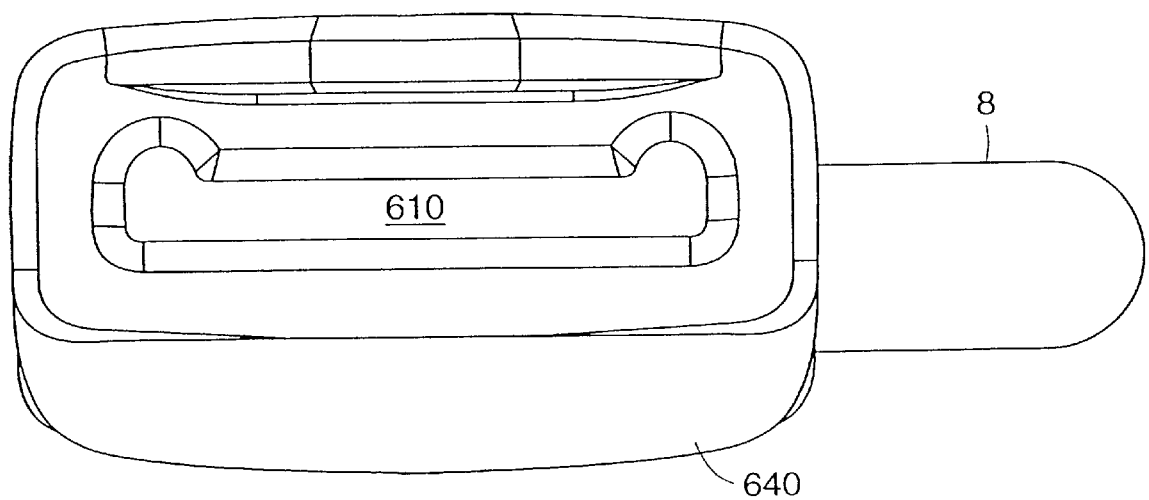
FIG. 9 is an end elevational view of the smart sensor receptacle showing the hinged door and the rail alignment channels.

FIGS. 7 and 8 illustrate several additional features of the mating receptacle 6. A cross section through the mating receptacle 6 perpendicular to the plane of the interface platform mounting surface is shown in FIG. 7. The opening into which the interface platform 4 is inserted is normally sealed by the hinged door 610 made of thermoplastic elastomer. The door 610 serves to bar liquids from entering the mating receptacle 6 when the interface platform 4 is not inserted, an important feature in a hostile environment such as an operating room. The action of inserting the interface platform 4 into the mating receptacle 6 pushes the door 610 open and out of the way. Liquids are further barred from entry into the receptacle by two wiping surfaces 620. These act to wipe off any liquid that may be on the surface of the interface platform 4 and which poses a potential short-circuit risk. These wiping surfaces 620 are part of the thermoplastic elastomer outer sleeve 640 of the mating receptacle 6. This soft sleeve 640 minimizes pressure indentations in a patient's skin when the mating receptacle 6 is positioned such that a patient is lying on it. Also visible in this view are the electrical contact points 638 for the exposed contacts of the printed conductors 53 and the electrical contact points 635 for the memory module contact pads 42. The hinged door 610 is normally held in the closed position. The electrical contact points are also shown from a different orientation in FIG. 8. FIG. 9 shows an end-on cross-sectional view through the hinged door 610 from the direction of the end of the mating receptacle 6 which accepts the interface platform 4. The rail alignment channels 650 receive the keyed alignment rails 485, ensuring proper alignment of the interface platform 4 as it is inserted into the mating receptacle.

Figure 10A:
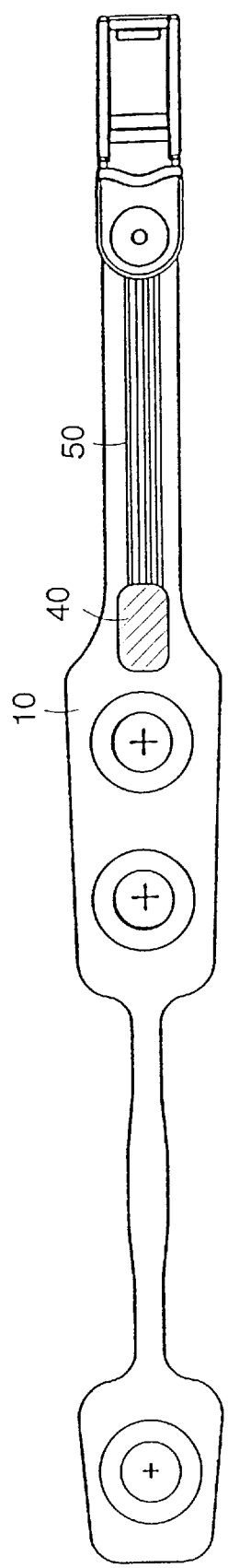
FIG. 10(a) is a top plan view and FIG. 10(b) is a bottom plan view of two alternate embodiments of the smart sensor in which the memory module is mounted on the top side and the underside of the flexible substrate respectively.
Figure 10B:
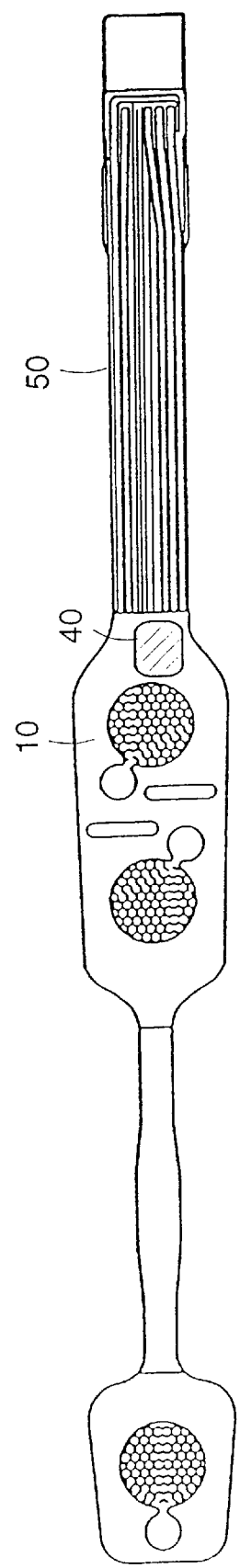

In an alternate embodiment shown in FIG. 10(*a*), the memory module 40 is mounted directly on the flexible substrate 10, opposite the side bearing the electrodes. In contrast to the preferred embodiment, the memory module 40 is mounted with its contact pads 42 against the flexible substrate 10. Additional printed conductors 50 are provided on the flexible substrate on the same side as the memory module 40 to connect the contact pads 42 of the memory module 40 to exposed contacts on the terminal tab 45 for connection to the monitor via a mating connector. The terminal tab 45 thus has exposed contacts on both sides. In this embodiment, the mating connector contains additional electrical contact points for the printed conductors electrically connected to the memory module 40 in place of contact points for the memory module contact pads 42. Alternatively, in the embodiment shown in FIG. 10(b), the memory module 40 is mounted on the same side of the flexible substrate 10 as the electrodes. This design simplifies the smart sensor construction by requiring printed conductors 50 on only one side of the flexible substrate 10. Adequate insulation must be provided, however, to protect the patient from a possible fault condition arising from the close proximity to the skin of the smart sensor current supply conductor.

Figure 11:
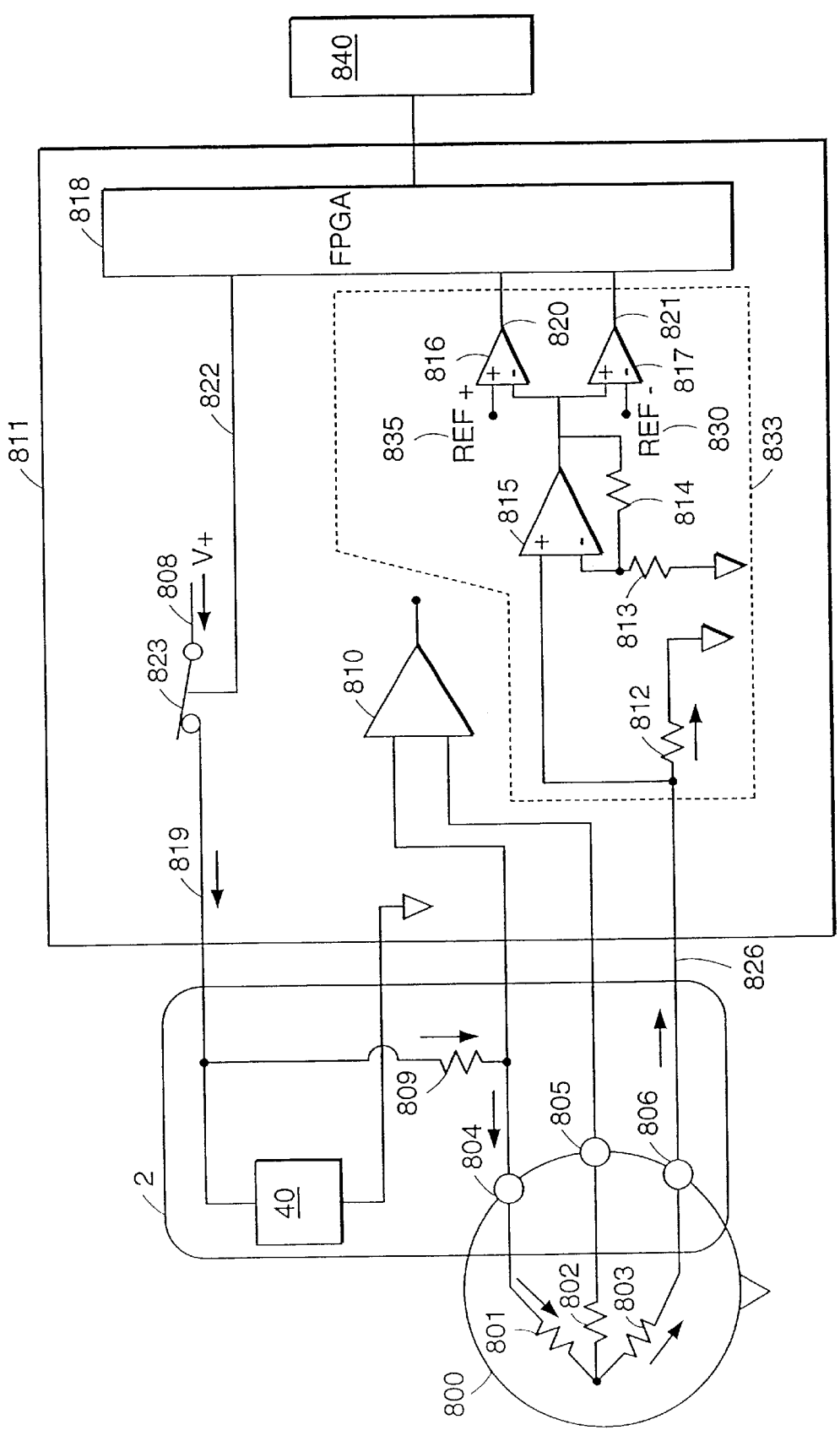
FIG. 11 is a schematic diagram of the ground fault detection circuit used in the smart sensor shown in FIG. 1.

Referring now to FIG. 11, the patient interface circuits 811 incorporate a ground fault detection circuit 833. In the event of a detected ground fault, the Field Programmable Gate Array (FPGA) 818 shuts down the power to the memory module 40. If the fault is still detected, the FPGA 818 then shuts down the power supplying the instrumentation amplifier 810 and alerts the monitor 840 that a shutdown has occurred. The sequential shutdown of first the memory module 40 and then the instrumentation amplifier 810 allows the monitor to localize the failure to either of these components. A hard re-boot is necessary to restore monitoring.

A potential single fault condition is the failure of the insulation between the smart chip power connection V+ 808 and one of the patient connections 804, 805. This could occur, for example, if the mating receptacle 6 were to be wet with a conductive solution such as saline. An electrical path represented by resistor 809 would form an electrical bridge between the memory module power line 819 and the patient connection, e.g. 804. Current would flow through the patient 800 as indicated by the arrows, traveling through patient connection 804, patient electrode impedances 801, 803, through ground electrode connection 806, and into the ground of the instrumentation amplifier 810. The International Electrotechnical Commission has set the maximum permissible current at 50 micro-amperes in a single fault condition, defined as "patient auxiliary current." Current in excess of this limit is detected in the present invention by using sense resistor 812 to convert the current flow from the patient to ground into a voltage. This current-proportional voltage is amplified by the circuit consisting of operational amplifier 815 and resistors 813, 814. Comparators 816, 817 compare the amplified current-proportional voltage to reference voltages 830, 835 and output digital signals 820, 821 which indicate whether or not the patient auxiliary current has been exceeded. Reference voltages 830, 835 are equal in magnitude, but of opposite sign; 835 is positive, 830 is negative with respect to ground. The magnitude of reference voltages 830, 835 is equal to the magnitude of the output voltage of operational amplifier 815 when the current through sense resistor 812 is 50 micro-amperes. If the polarity of the current through sense resistor 812 is positive, signal 820 will be at the negative saturation voltage of comparator 816 if the output voltage of amplifier 815 is greater than reference voltage 835, and at the positive saturation voltage of comparator 816 if the output voltage of amplifier 815 is less than reference voltage 835. Similarly, if the polarity of the current through sense resistor 812 is negative, signal 821 will be at the positive saturation voltage of comparator 817 if the output voltage of amplifier 815 is greater than reference voltage 830, and at the negative saturation voltage of comparator 817 if the output voltage of amplifier 815 is less than reference voltage 830. Thus, currents in excess of 50 micro-amperes are detected by the condition of either of signals 820, 821 being low, as detected by the Field Programmable Gate Array (FPGA) 818. In the event of detection of auxiliary current in excess of the detection threshold, the FPGA 818 responds by de-asserting signal line 822, signaling switch 823 to disconnect power to the memory module 40. Thus the power to the memory module 40 is disconnected and the auxiliary current ceases. FPGA 818 then notifies the monitor 840 of the event. The monitor causes an error message to be displayed on the monitor display, signaling the user to rectify the condition. A button on the monitor must be pressed for operation to continue; this button initiates a hard re-boot of the entire monitor system.

If the source of the current were something other than the smart sensor power line 819 the fault would continue to be detected even after switch 823 is opened. In such a case FPGA 818 notifies the monitor 840, which shuts off power to the patient interface circuits 811, causing the current to cease. The monitor displays an error message signaling the operator to rectify the condition. The monitor software must be re-booted for operation to continue.

Although the ground fault detection circuit 833 in the preferred embodiment is only in the patient ground circuit, those skilled in the art will recognize that any patient connected circuit could contain a fault sensing circuit.

Figure 12:
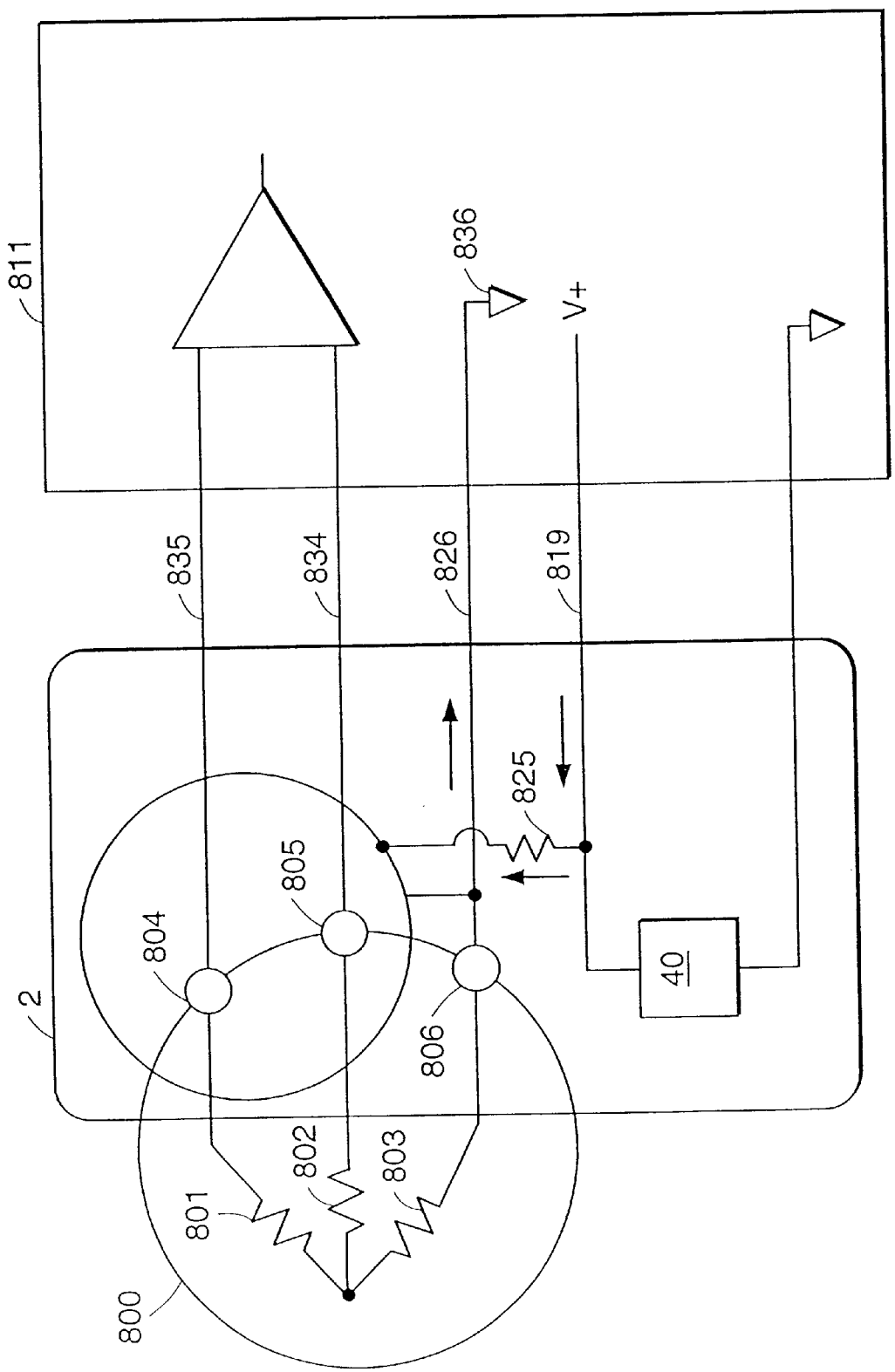
FIG. 12 is a schematic diagram of the ground guard protection circuit used in the smart sensor shown in FIG. 1.

Referring now to FIG. 12, the patient interface circuits 811 incorporate a ground guard conductor 55 that surrounds the patient-connected conductors 834, 838. In the normal operating condition, insulation is achieved between the memory module power conductor 819 and the patient conductors 834, 838 by physical separation. This insulation can be compromised in a fault condition such as the wetting of the connector with a conductive solution such as saline, which may result in current flowing from the memory module power conductor 819 into the patient-connected conductors 834, 838. To prevent this condition, an exposed electrical guard conductor 55 is interposed between the memory module power conductor 819 and the patient-connected conductors 834, 838. In a fault condition, an electrical path represented by resistor 825 would then form an electrical bridge between the power line 819 and the guard conductor 55. Current would flow as indicated by the arrows from the memory module power line 819, through the bridge 825 into the ground guard conductor 55 and though the ground conductor 826 into the patient interface circuit ground 836. Thus the current would be shunted harmlessly away from the patient.

It can be seen that the guard combined with the ground fault detector would enable the system to detect any condition that compromises the insulation in the sensor. One such condition is the wetting of the sensor. Thus the preferred embodiment comprises a wetness detector for the sensor connector.

Figure 13:
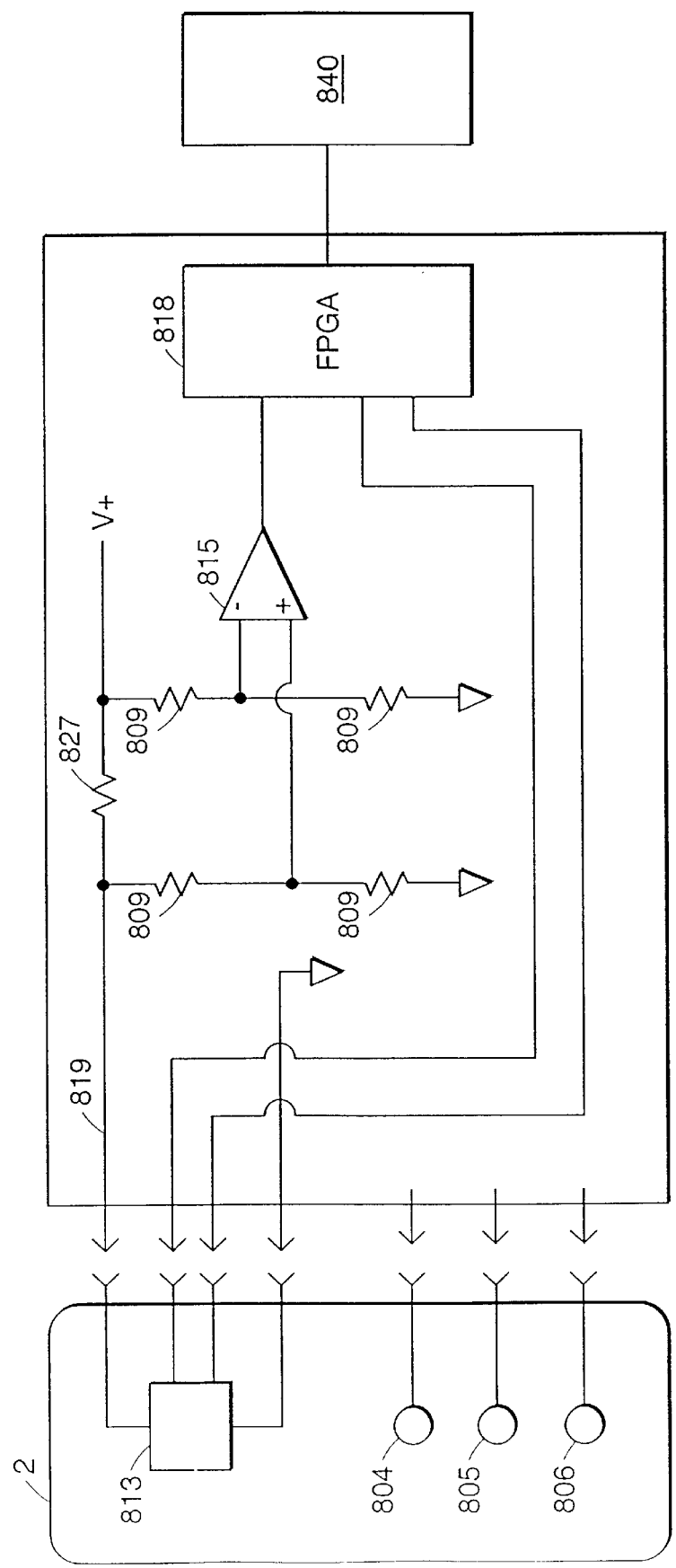
FIG. 13 is a schematic diagram of the smart sensor connection detection circuit.

Referring now to FIG. 13, the method for detecting the connection of the smart sensor to the monitor will now be described. The presence or absence of the connection of a smart sensor 2 to the patient interface circuits 811 is detected by monitoring the electric current flow in memory module power line 819. This current also flows through resistor 827, creating a voltage that is sensed by comparator circuit 832. In the absence of a connection of a smart sensor 2 to the patient interface circuits 811, no electric current flows in memory module power line 819. The resistors 828, 829, 831, 837 are selected such that in the case of no current flow in memory module power line 819, there will be negligible current flow through resistor 827, and further such that the voltage at the negative (−) input to the comparator 832 is less than the voltage at the positive (+) input of the comparator 832. In this state, the comparator outputs a logic high to FPGA 818. Upon connection of the smart sensor 2 to the patient interface circuits 811, electric current flows in memory module power line 819. This increases the current flow through resistor 827, the relative voltages at the input to the comparator 832 reverse and the comparator outputs a logic low, indicating the presence of the smart sensor. The FPGA 818 notifies the monitor 840, which then initiates the authentication sequence.

Figure 14:
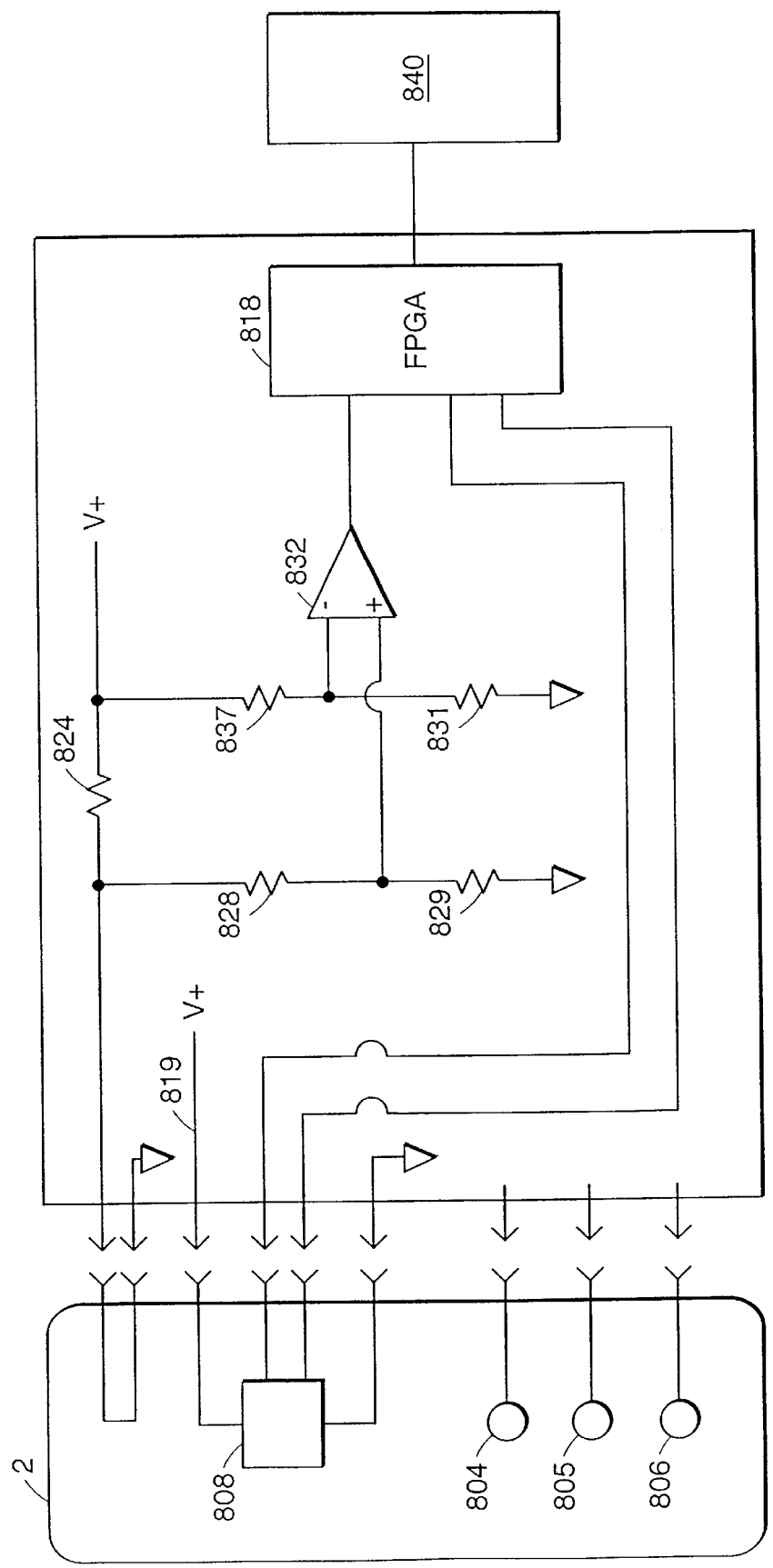
FIG. 14 is a schematic diagram of an alternate embodiment of the smart sensor connection detection circuit.

Referring now to FIG. 14, an alternate embodiment to detect the connection of a smart sensor 2 to the patient interface circuits 811 makes use of a dedicated conductor loop 839 in the smart sensor, each end of which connects to contacts in the mating receptacle. One of these contacts would be connected to the voltage supply of the monitor through a current limiting and sensing resistor 824, the other would be connected to ground. Current flow through the resistor 824 is detected using the comparator 832 and the resistors 828, 829, 831, 837, whose values are selected in the manner described above so that the output of comparator 832 is a logic high when no smart sensor is connected and a logic low when a smart sensor is connected, causing current to flow.

The smart card memory module 40 is preferably of the type designed for use in pre-paid phone cards, in which the security of the data on the card is of paramount importance. Examples of suitable memory modules are the SLE 4436 manufactured by Siemens AG, Munich, Germany, or alternately the type PCF2036 manufactured by Phillips Electronics NV, Amsterdam, The Netherlands. The memory on such modules is divided into 3 segments; ROM, PROM, and EEPROM, including a counter. These modules provide for memory retention for at least 10 years without power application.

Smart card technology provides unique benefits in this application; such modules are ideally suited to this invention due to the inherent security provided by its design and operation. The small size of the smart card memory module die (1 mm$^2$) ensures that flexing of the interface platform 4 will not fracture it. In addition, the physical layout of the wire leads from the die make it difficult to physically or electrically probe the module (e.g., with an oscilloscope) in order to sample the bi-directional transmitted data. As a further security measure, the smart card memory module 40 is shipped to the manufacturer in a locked state to provide security during delivery. In the locked state, it is not possible to read from or write to the memory module 40; the smart sensor manufacturer using a transport code generated by the manufacturers of the smart card module must first enable it. The smart sensor manufacturer unlocks the memory module 40 during the programming stage of the manufacturing process. Further, once the memory module 40 is relocked, it may be written to only once (with the exception of the counter). This provides an additional layer of security, as the data on the memory module 40 cannot subsequently be changed. Those skilled in the art will recognize that many different smart card-type memory modules 40 may be used in its place.

The manufacturer of the smart card memory module 40 also writes a binary data string referred to as a Manufacturer Code to a read-only (ROM) area of the memory module 40. This code is unique to those memory modules 40 sold to the purchaser (the manufacturer of the smart sensor 2) and only that purchaser (the smart sensor manufacturer) may purchase modules containing this code. Because this code is in ROM, it may not be altered and thus serves as an identifier of the source of products containing the smart card memory module.

The use of a smart card memory module 40 is further differentiated from a typical semiconductor memory device (e.g., an SGS-Thomson ST24C02, a 2 Kilobit EEPROM) by a different communication protocoL The difference in protocols between the smart card memory module 40 and an EEPROM prevents the construction of a counterfeit smart sensor using a non-smart card memory module 40.

A further advantage of the smart card memory module 40 is that a portion of the counter memory is PROM. In order to facilitate the stored value applications for which the smart card memory module 40 is designed, a portion of the counter memory space is read only PROM. The initial value in the PROM is set during manufacturing programming. During subsequent use, individual bits of the PROM may be set to zero, but cannot be reset to 1. The remainder of the counter is EEPROM and again, the initial value is set during manufacturing programming. Like the PROM, during subsequent use individual bits of the EEPROM may be set to zero. Additionally, the EEPROM may be reset to a 1's by writing to the PROM.

A portion of the EEPROM section is designated as a usage counter to track the number of times the smart sensor 2 has been authenticated, each bit representing one use. In the preferred embodiment, 16 bits are used. These bits are set to 1's during manufacturing programming. In addition, a bit within the PROM is used to indicate whether the smart sensor 2 has been used the maximum number of times (the use bit); this bit is set to 1 during programming.

During each smart sensor authentication process, the monitor verifies that the PROM use bit is set to a 1 and that the number of remaining uses, as represented by the number of usage counter bits set to 1, is greater than zero. Each time the smart sensor 2 is successfully authenticated, one of the usage counter bits is set to zero, decrementing the number of allowable uses by one. The usage counter bits are set to zero starting with the least significant and progressing to the most significant. When the last usage counter bit is set to zero (after 16 uses in the example), the monitor writes to the PROM use bit, setting it to zero and resetting the usage counter bits to 1's. This effectively prevents the subsequent use of the smart sensor 2 (beyond the present use), since the condition that the PROM use bit be 1 will fail Further, since it is not possible to reset the use bit to a 1, the usage counter cannot be "reloaded".

Numerous pieces of data are written to the smart sensor 2 during the manufacturing process. This data includes, but is not limited to, a key code, an OEM code, a lot code (incorporating the date of manufacture), a shelf life code, a sensor type code, and serial number. In addition, part of the memory module counter is configured as a usage counter, and is set to the maximum number of allowable sensor uses, preferably 16 in the current embodiment. Together with the manufacturer code, this data is collectively referred to as the device data.

In order to protect the integrity of the smart sensor 2, some of the device data is encrypted before it is written to the smart sensor 2. The encryption process and the related generation of a digital signature are integral features of the smart sensor 2, which protect it from counterfeiting by an unauthorized source. In general, encryption systems operate by using a specific mathematical algorithm to scramble a data sequence or "message" so that the contents of the message are unintelligible unless that message is decrypted by a related algorithm. A security key encryption algorithm is one that uses a "key" (E), a specific alphanumeric sequence that determines how the algorithm scrambles the message. Thus, for a specific data sequence or "message" (M), the encrypted message C is generated by applying the encryption algorithm $f_e$ to the message M using the key E.

$$C=f_e(E,M)$$

The original message M may be recovered from the encrypted message C by applying the related decryption algorithm $f_d$ to C using the decryption key D.

$$M=f_d(D,C)$$

There are two general classes of encryption algorithms, symmetric and asymmetric. Symmetric algorithms use the same key for encryption and decryption; that is, E=D. Asymmetric algorithms use different encryption and decryption keys. Symmetric algorithms are typically computationally less intensive but have the weakness that the same key is used both to encrypt and decrypt the message. Thus knowledge of the decryption key and of the decryption algorithm (both of which might be obtained by reverse engineering the monitor software) would allow a potential counterfeiter to produce smart sensors with validly encrypted device data.

A particular class of asymmetric encryption algorithms are the Public Key algorithms. In these algorithms, the encryption and decryption keys are a mathematically related pair, but the mathematical relationship between the keys is such that it is not possible to derive one of the keys from knowledge of the other key. Thus, one key (the "Public" key) may be made public knowledge without compromising the security of the other key (the "Private" key). In the case of the present invention, the public key is embedded in the monitor software and used to decrypt the data, while the private key is used to encrypt the data and is kept secret by the smart sensor manufacturer.

It would seem that public key encryption would provide an authentication of the source of the smart sensor, since if it is possible to properly decrypt the message using the monitor's public key, it must have been encrypted by the related private key, the only possessor of which is the smart sensor manufacturer. However, the only test in this case of whether a decryption is "proper" is whether the message is meaningful. Given the relatively simple nature of binary codes (as opposed to natural text), the possibility that an incorrect decryption might be accepted as correct is relatively high. This might result from the use of an incorrect key for encryption or decryption, or the corruption of the message stored on the smart sensor. Thus, while encryption provides message confidentiality, it does not provide authentication of the source of the message, nor does it provide authentication of the integrity of the data.

The source of the smart sensor 2 is authenticated and the integrity of its data validated by using a "digital signature." Signature generation requires the use of a "hash" function (h), which operates on a message to produce an output sequence that is specific to the content of the message itself. If the message M changes, so will the hashed message h(M). In the case of a public key algorithm, the digital signature (S) is generated using a signature generation function $f_s$, which typically uses both the private (E) and public (D) keys as well as the hashed message h(M). The signature is typically made up of 2 data sequences, $S_1$ and $S_2$.

$$(S_1,S_2)=f_s(E,D,h(M))$$

The message M is encrypted using the private key. The encrypted message C is then written to the smart sensor 2 along with the digital signature ($S_1,S_2$). Upon reading the data from the smart sensor 2, the monitor first decrypts the message using the public key to obtain M. The digital signature is then verified by the signature verification function $f_v$, which first applies the hash function to M and then uses h(M) in conjunction with the internally stored public key (D) and the components of the signature to verify that the derived value is equivalent to one of the signature components.

$$S_2 \equiv f_v(D,S_1,S_2,h(M))$$

If this equality is true, the signature is validated. This will occur if and only if the public key D and the private key E used to encrypt the data are the unique related pair and if the message M used to verify the signature is the same as that used to generate the signature. Thus, if the signature can be verified, it must have been generated using the unique private key that corresponds to the public key used for the verification. Since the only holder of the correct private key is the authorized smart sensor manufacturer, successful signature verification ensures that the smart sensor 2 indeed originated at an authorized source. In addition, the successful verification of the signature means that the message used to verify the signature must be the same as that used to create the signature (otherwise h(M) would be different). Thus, successful verification of the signature validates the integrity of the data stored on the smart sensor 2.

During the monitor manufacturing process, a particular public key is embedded within the monitor software. Separately, during the smart sensor 2 manufacturing process, the device data corresponding to each smart sensor 2 is first formatted as a single binary sequence, referred to as the device data string. The device data string corresponding to each smart sensor 2 is encrypted using the public and private keys and the Public Key encryption algorithm. Each encrypted device data string is thus unique since it includes the smart sensor 2 serial number. In addition, both the public and private keys are in conjunction with the device data string to generate a digital signature. The digital signature is also formatted as a binary sequence. After the smart sensor memory module is unlocked using the transport code in the course of its manufacture, the encrypted binary device data string and the binary digital signature are combined to form a single binary sequence (the sensor data string) which is written to the memory module.

| | | Device Data String: | | | | |
|---|---|---|---|---|---|---|
| Manufacturer Code | Key Code | OEM Code | Lot Code | Shelf Life | Sensor Type | Serial Number |
| | | Sensor Data String: | | | | |
| Device Data String | | | | Digital Signature | | |

Use of a public key algorithm provides a significant defense against smart sensor counterfeiting. Even if a potential counterfeiter obtained the public key and the decryption algorithm by reverse engineering the monitor software, a valid digital signature could not be generated without the private key. The private key is used only in the manufacturing process and is not stored in the monitor software; thus, it is not available to the counterfeiter. Further, the private key cannot be easily computed from the public key. If either the key or the encryption algorithm becomes compromised, the smart sensor manufacturer may, by issuing a new revision of monitor software, expire existing keys and issue new keys to the existing installed monitor base to minimize any possible security impacts.

Multiple public/private key pairs may be used to provide different decryption keys for smart sensors distributed by different OEMs. The decryption key in use is coded by the key code, which is stored in the smart sensor memory. The public keys corresponding to each of the stored key codes may be integrated into the monitor software. The authentication program will use the key code to either determine the correct public key to be used for decryption and digital signature validation before the decryption process begins or to promptly expire a key.

Efforts to "break" the encryption code and determine the private key are exceedingly computationally intensive, and a successful effort would yield only the single private code currently in use. When the key pair in use is changed, the "code breaking" effort would have to be repeated to obtain the new private key. For this reason, security can be greatly enhanced by changing the public/private key pairs at regular intervals. To this end, the smart sensor system allows for regular changes in the set of public keys in use by the authentication program by subsequent updates to the monitor software. The private key is changed in the manufacturing process, and this change is reflected in the key codes.

Various public key encryption algorithms are well known in the state of the art, such as those implementing the RSA algorithm described by R. L. Rivest, A Shamir, and L. M. Adleman, in "A Method for Obtaining Digital Signatures and Public-Key Cryptosystems", Communications of the ACM, volume 21, pages 120–126, February 1978 and the Discrete Logarithm algorithm described by T. ElGamal, in "A public key cryptosystem and a signature scheme based on discrete logarithms", Advances in Cryptology—Proceedings of CRYPTO'84, Springer Verlag Lecture Notes in Computer Science 196, pages 10–18, 1985. Further, digital signature algorithms are similarly well known in the state of the art, such as the Digital Signature algorithm (DSA) described in National Institute of Standards and Technology, "Digital Signature Standard", FIPS Publication 186, 1993 and the improved ElGamal algorithm described by C. P. Schnorr in "Efficient signature generation by smart cards", Journal of Cryptology, volume 4, pages 161–174, 1991. However, those skilled in the art will recognize that any public key encryption/decryption method and digital signature method may be used.

While the embodiment described above utilizes the encryption of the data message written to the smart sensor 2, it is recognized that the digital signature method will function equivalently well if the message is written to the smart sensor 2 in unencrypted form, or alternately if the message is written in hashed form.

Figure 15:
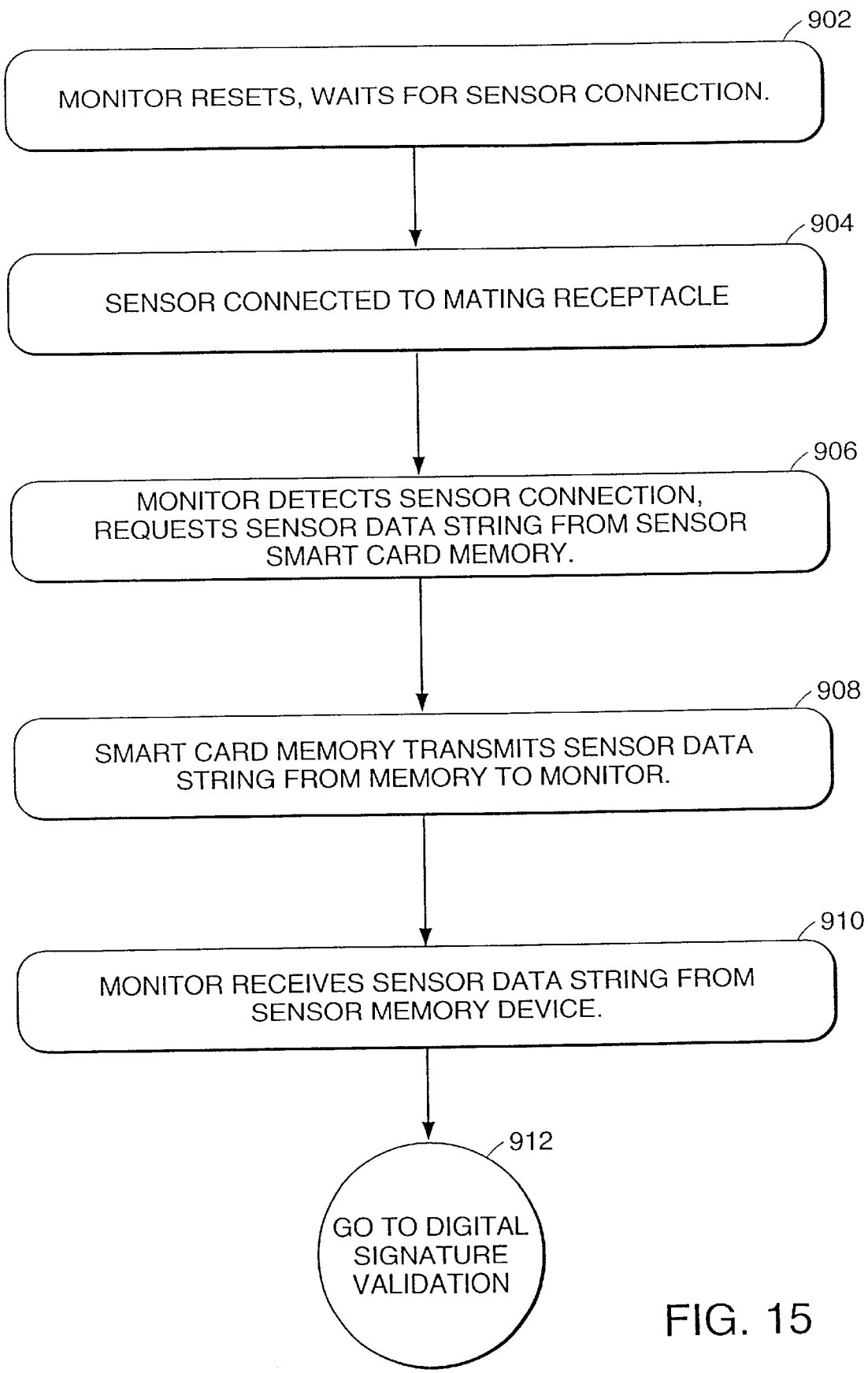
FIG. 15 is a flowchart of the data string acquisition routine used by the smart sensor shown in FIG. 1.

Referring now to FIG. 15, the algorithm used by the monitor to authenticate the smart sensor 2 will now be described. Each time the smart sensor 2 is disconnected from and reconnected to the same or a different monitor or each time the monitor is restarted, the monitor first resets the data string acquisition routine and waits for the detection of a smart sensor connection at the mating receptacle 6 in step 902. The detection is performed by the monitor's sensor interface electronics, shown in FIG. 13. It consists of a current sensing circuit that monitors the current in the power conductor of the smart sensor memory module 40. Upon detection of a smart sensor connection in step 904, the data acquisition routine interrogates the smart sensor in step 906, requesting that the smart sensor 2 transmit the stored sensor data string. The smart sensor 2 responds to this request by sending the sensor string to the monitor in step 908. After receiving the sensor data string from the smart sensor 2 in step 910, the data acquisition routine passes the string to the digital signature validation routine in step 912.

Figure 16:
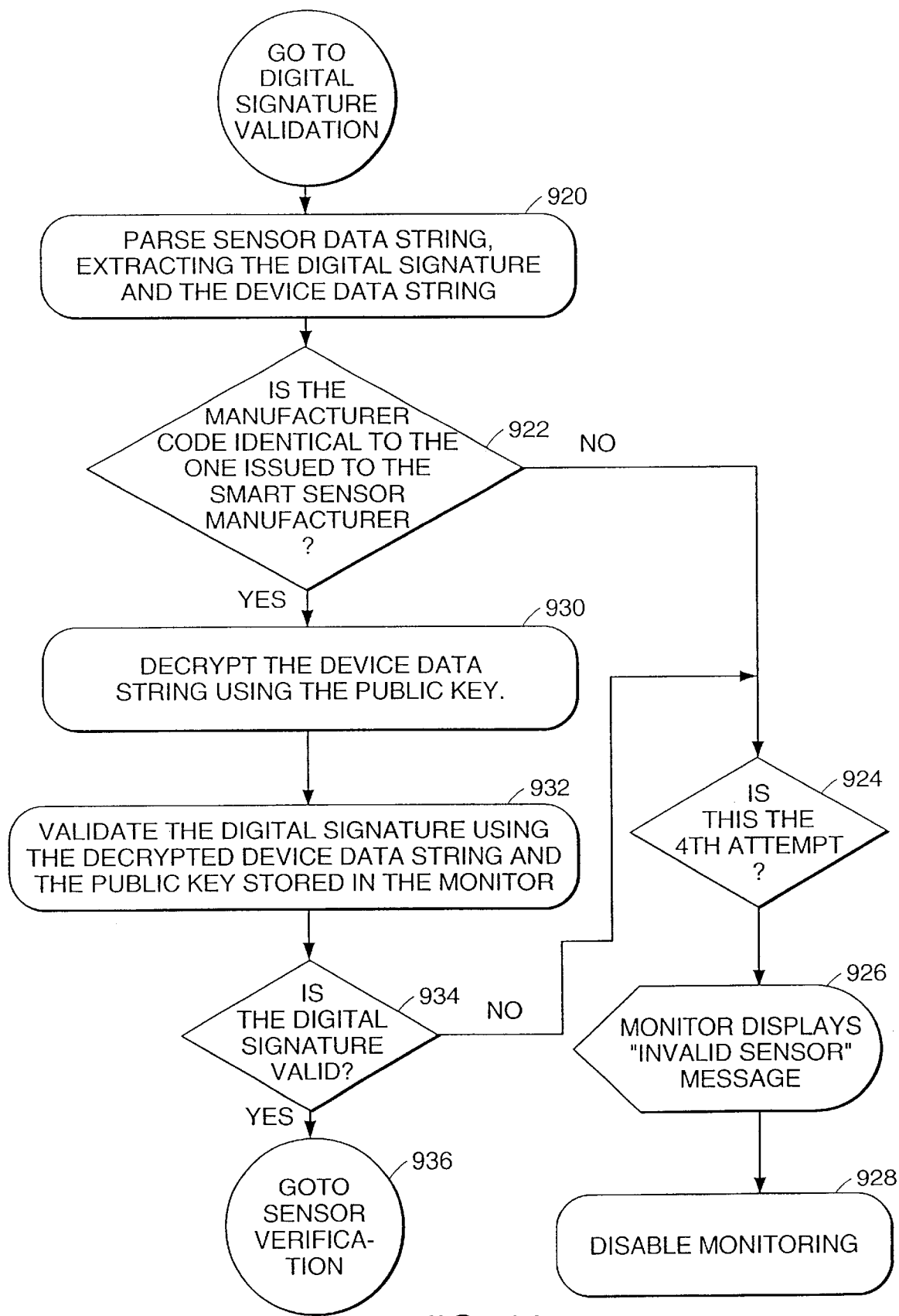
FIG. 16 is a flowchart of the digital signature validation algorithm used by the smart sensor shown in FIG. 1.

Referring now to FIG. 16, the digital signature validation routine first parses the sensor data string into its constituent parts, the digital signature string and the device data string in step 920. Then in step 922, it uses the manufacturer code to verify the smart sensor memory module 40 is one that was purchased by the smart sensor manufacturer. If this condition is not met, the test is repeated up to 3 more times in step 924. After the fourth failure, a message indicating that the connected sensor is an illegal device is displayed on the monitor screen in step 926 and the monitor will terminate the authentication program and refuse to proceed with data collection in step 928. If the manufacturer code is determined in step 922 to be valid, the digital signature validation routine uses the decryption algorithm and the embedded public key to decode the device data string in step 930. In step 932, the system next validates the digital signature using the validation algorithm, the device data string and the embedded public key. The validation algorithm then determines, in step 934, whether or not the signature is valid, and thus produced by an authorized source. If valid, the signature is accepted; if not, validation is attempted up to 3 more times 16. If the validation fails 4 times, the monitor displays a message on its screen indicating to the user that monitoring will not proceed in step 926 and monitoring is disabled in step 928. Upon acceptance of the signature, program control is then transferred to the Sensor Verification Check in step 936.

Figure 17:
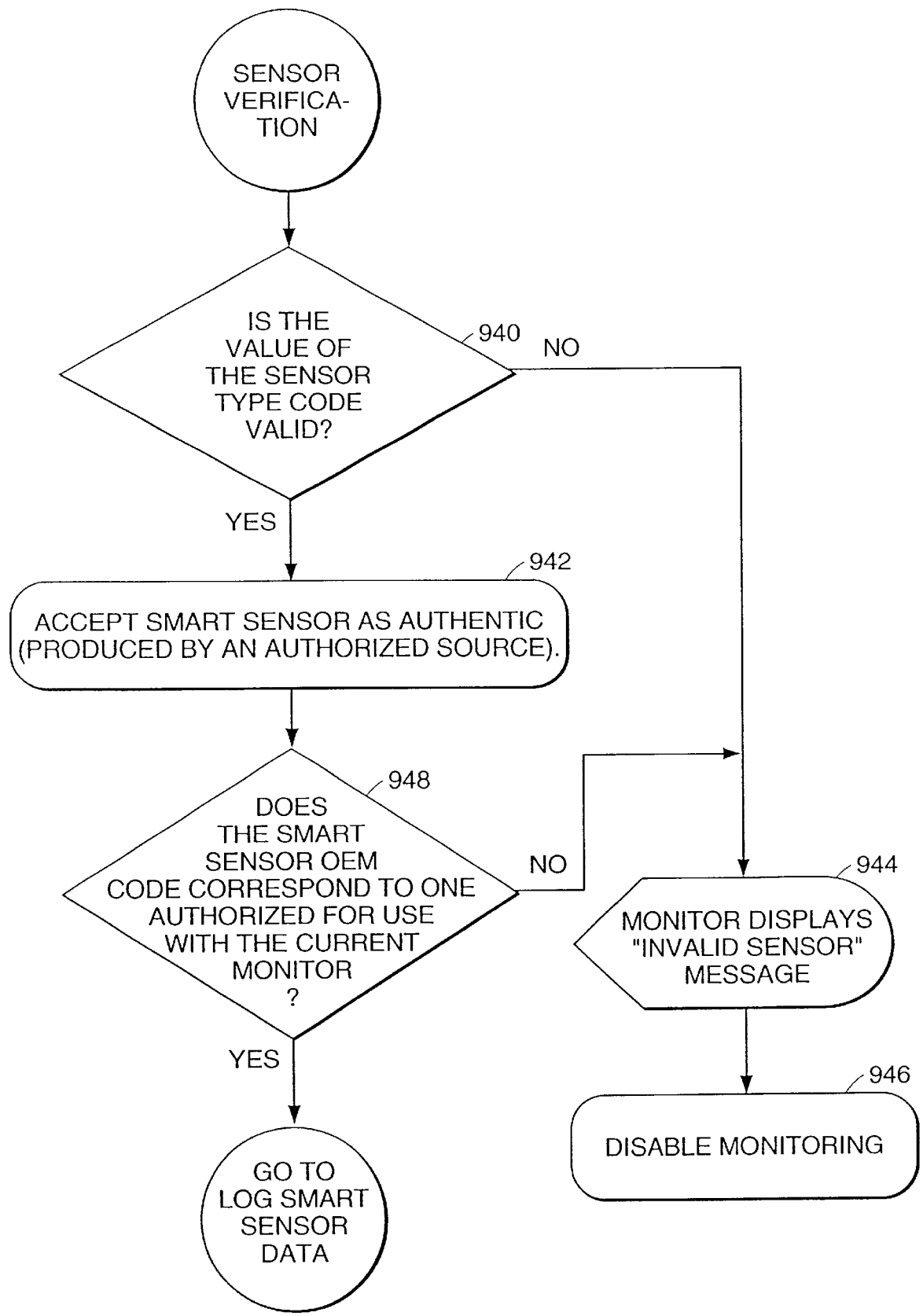
FIG. 17 is a flowchart of the verification algorithm used by the smart sensor shown in FIG. 1.

Referring now to FIG. 17, in step 940, the authentication software verifies that the value of the sensor type code corresponds to one of the possible values stored in a look-up table in the authentication software. If the sensor code is a valid value, then the smart sensor 2 is accepted as authentic in step 942. Otherwise, a message indicating that the connected sensor is an illegal device is displayed on the monitor screen in step 944 and the monitor will terminate the authentication program and refuse to proceed with data collection in step 946.

It is anticipated that while the smart sensor 2 will be made by a single manufacturer or various authorized subcontractors, different versions of the monitor may be manufactured or distributed by different licensed manufacturers (OEMs) using the smart sensor interface circuit 811 and monitoring software supplied by the smart sensor manufacturer. The OEMs may also distribute smart sensors. It is therefore desirable to allow only smart sensors distributed by a specific OEM to be used with the monitors manufactured by the same OEM. The identity of the distributor will be encoded in the smart sensor 2 in the OEM code. If the smart sensor's manufacturer code is determined to be valid in step 942, the authentication software, in step 948, next checks the OEM code against a look-up table to determine whether that OEM code is allowed to be used with the specific monitor. If the particular smart sensor 2 is not authorized for use with the particular monitor, a message to that effect is displayed on the monitor screen in step 944 and the monitor will terminate the authentication program and refuse to proceed with data collection in step 950.

The monitor maintains a log of the set of smart sensor parameters in its internal nonvolatile memory, with a separate entry for each smart sensor 2 which has been authenticated by a given monitor, as determined by the smart sensor serial number and lot code. The logged parameters include the current date and time, the sensor type, the OEM code, and the smart sensor serial number and lot code. A usage counter is also associated with each entry in the log. Sufficient memory is reserved in the nonvolatile memory for this purpose to enable the log to contain entries from some large number of smart sensors 2 (200 in the preferred embodiment); when the log is full, the oldest entry is deleted to create memory space for the newest entry. A representative of the manufacturer may download the sensor usage log onto a personal computer. The manufacturer may use this data to resolve quality control issues.

Figure 18:
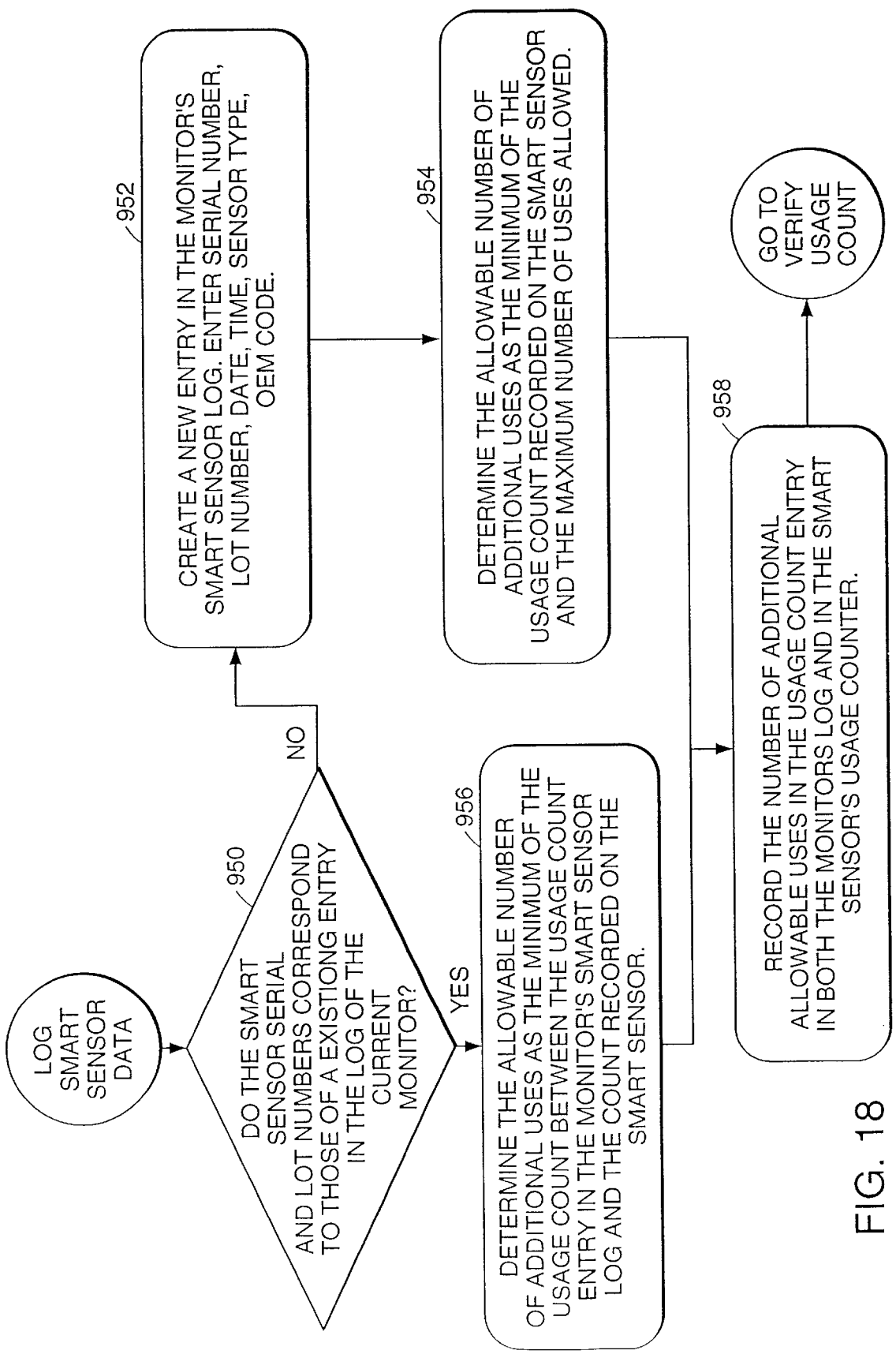
FIG. 18 is a flowchart of the data logging algorithm used by the smart sensor shown in FIG. 1.

Referring now to FIG. 18, if the smart sensor OEM code is one that is authorized for the particular monitor, the authentication software checks if a record in the log has the serial number and lot code of the current smart sensor 2 in step 950. If so, the existing record is used for the currently connected smart sensor. If such a record does not exist, a new log entry is created and its fields are loaded with the data values obtained from the device data string in step 952. The current date and time are also recorded. After creation of the record or if such a record does exist, the monitor software next updates the usage counters.

The smart sensor 2 is designed to be disposable and therefore re-use of a smart sensor 2 on a different patient may degrade performance, as well as posing a potential infection risk. However, limited reuse must be allowed, as a smart sensor 2 may be disconnected and reconnected to the same or a different monitor several times in order to accommodate patient movement, transfer, etc. The monitor therefore utilizes the usage counter in each record in the log to determine whether a particular smart sensor 2 has been used more than an allowable number of times and also to warn the user of the reuse status of the connected smart sensor.

The usage counter in the smart sensor 2 and that in the log of the monitor to which the smart sensor 2 is connected are maintained as mirror images. By maintaining the usage counter in the smart sensor 2 memory as well as in the monitor memory, the integrity of the usage count is preserved when the smart sensor 2 is disconnected and then reconnected to a different monitor. This would occur, for example, when a patient who was first monitored in the operating room was transferred to an intensive care unit (ICU) where monitoring was to be continued using a different monitor. If the smart sensor 2 and monitor usage counters contain different counts for the same smart sensor serial number and lot code, as would occur when a previously used smart sensor 2 is reconnected to a different monitor, both counters are reset to the value of the counter indicating the smallest number of remaining uses.

After logging the smart sensor data, the authentication software, in step 954 first synchronizes the usage counters by determining the number of remaining allowable uses and writing that value to the usage counters maintained in the monitor's smart sensor log and on the smart sensor 2. If a new record has just been created for the current smart sensor 2 (identified by serial number and lot code), the number of remaining allowable uses is calculated as the minimum of the value in the usage counter of the connected smart sensor 2 and the maximum number of allowable uses. If there is a pre-existing record in the log with the same serial number and lot code as that of the currently connected smart sensor 2, the number of remaining allowable uses is calculated as the minimum of the value in the usage counter of the monitor's smart sensor log and the value of the usage counter on the connected smart sensor 2 in step 956. The usage count field in the log and the usage counter in the smart sensor 2 are then both updated with the calculated number of remaining allowable uses in step 958.

Figure 19:
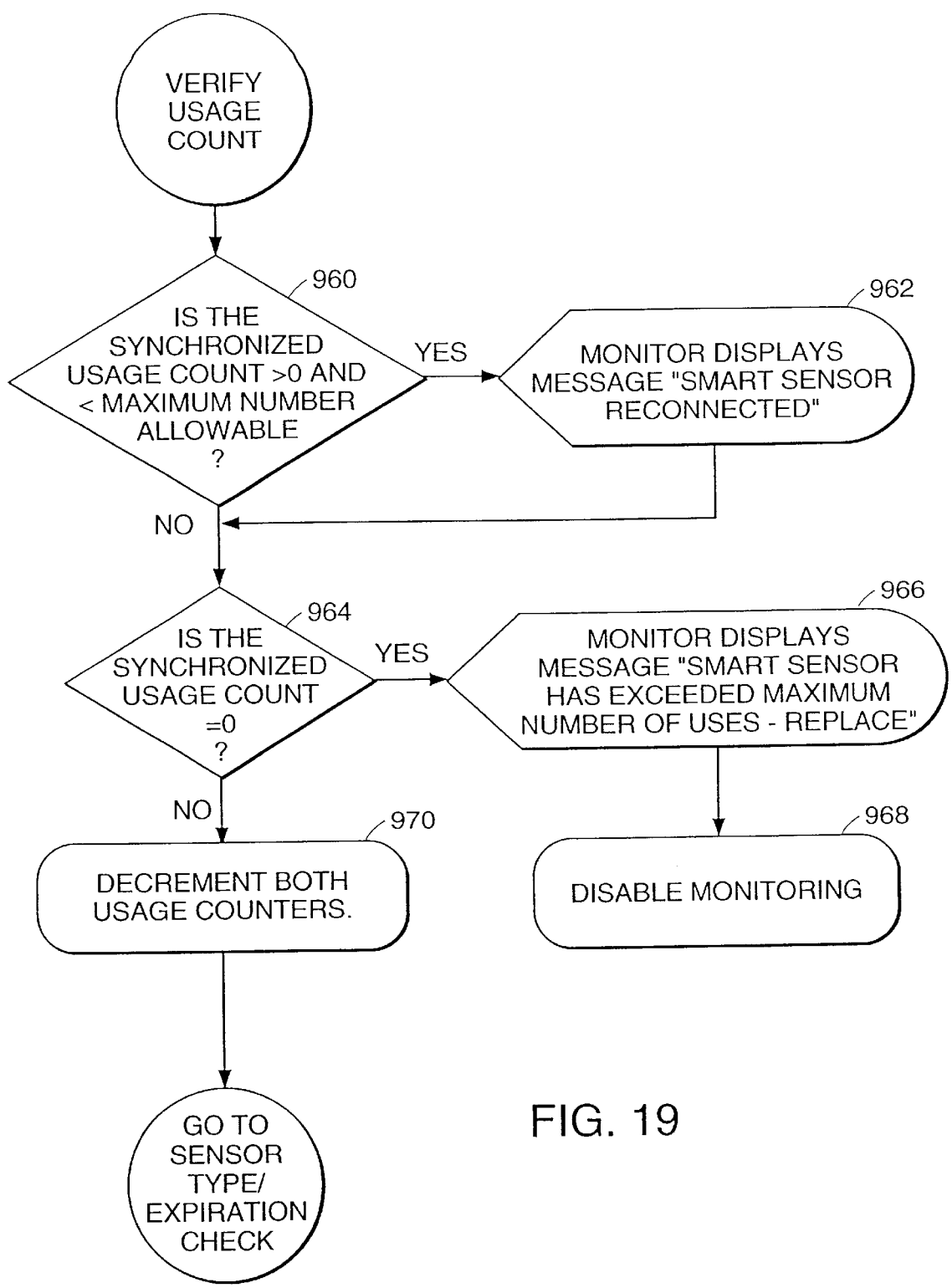
FIG. 19 is a flowchart of the usage count verification algorithm used by the smart sensor shown in FIG. 1.

Referring now to FIG. 19, in step 960 the authentication software next tests whether the value of the synchronized usage counters (the number of uses remaining) is less than the maximum number allowable but greater than 0; if so, the monitor will display a message to the user in step 962 with the number of previous uses and will warn that the performance of the smart sensor 2 may be unreliable. The authentication software then tests whether the value of the synchronized usage counters is zero in step 964. If so, the maximum number of uses has been reached and the monitor will alert the user in step 966 and disallow the use of the smart sensor 2 in step 968. If the usage counter is greater than zero, the authentication software will decrement both usage counters in step 970. This sensor usage check thus prevents a smart sensor 2 from being used more than the allowable number of times, regardless of which monitor the smart sensor 2 has been connected to. This outcome is obtained even if the usage counter on the smart sensor 2 was reset to the initial value by an unauthorized method; the actual number of times that smart sensor 2 has been used is logged in the monitor and will be reloaded onto the smart sensor 2 when it is reconnected.

In the preferred embodiment, different electrode configurations on the electrode array may require the use of different processing algorithms. In addition, different algorithms might be used with the same electrode configuration for different applications, such as surgical monitoring, monitoring in the intensive care unit (ICU), or monitoring pediatric patients. This information may be coded as a numeric value in the sensor type code on the smart sensor 2.

Figure 20:
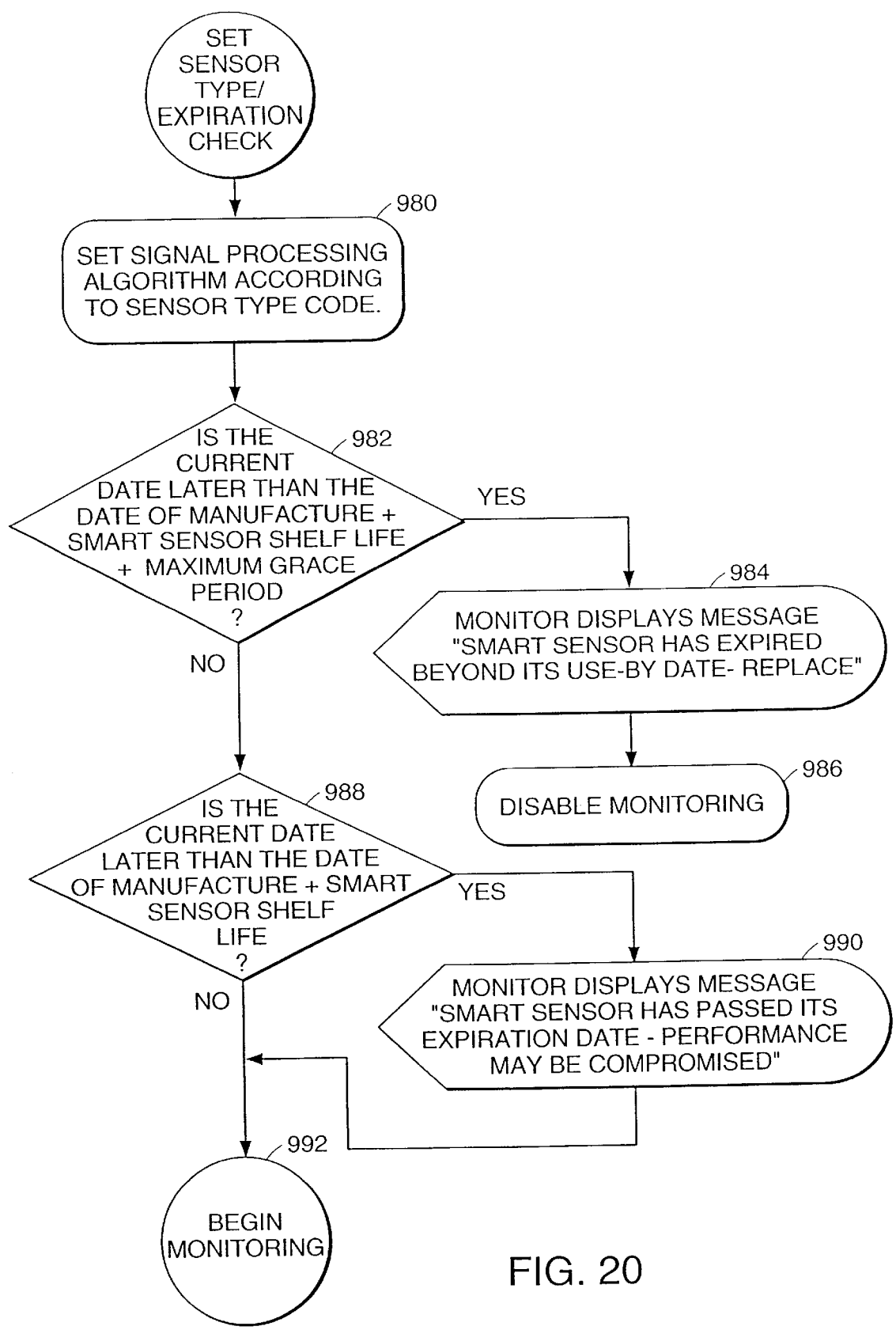
FIG. 20 is a flowchart of the type and expiration check algorithm used by the smart sensor shown in FIG. 1.

Referring now to FIG. 20, the monitor uses the sensor type code to select one of several internal processing algorithms appropriate to the specific smart sensor 2 and application in step 980. The sensor type code may also be used to switch the inputs to the monitor's instrumentation amplifiers if a signal is to be multiplexed.

The monitor next conducts a sensor expiration check. In step 982, the monitor compares the current date to the date of manufacture plus the shelf life (both read from the smart sensor memory module 40) plus a preset "grace period" to determine if the age of the smart sensor 2 is significantly greater than its recommended shelf life. If so, the monitor will display a message in step 984 directing the user to replace the sensor and will disallow use of the smart sensor 2 in step 986. The grace period is a preset time period, preferably one month, used to allow use of a smart sensor 2 after duly notifying the user of the potentially impaired performance. If the monitor determines in step 988 that the smart sensor 2 is beyond its expiration date, but not beyond the grace period, the monitor will display a warning to that effect on its display in step 990 before proceeding with monitoring in step 992.

A particular alternate embodiment of the smart sensor system uses the smart sensor memory module 40 as a means of customizing software in the monitor 840. In the case in which the monitor 840 calculates a diagnostic index in the manner taught by Chamoun, et aL in U.S. Pat. 5,458,117 which is assigned to the assignee of the present application and the teachings of which are incorporated herein by reference, the index coefficients may be stored in the smart sensor memory module 40 and transferred to the monitor 840 during the configuration procedure. These coefficients would then be used by the monitor 840 to calculate the diagnostic index Specific smart sensors intended for different applications may have different sets of coefficients stored in their memory modules during the manufacturing process. For example, in the case of a monitor which computes a diagnostic index quantifying the effect of anesthetic agents on the electroencephalogram, one model of smart sensor may be loaded with a first set of coefficients optimized for adult surgical use, a second model of sensor might be loaded with a second set of coefficients optimized for pediatric surgical use, and a third model of sensor might be loaded with a third set of coefficients optimized for use on adults in an intensive care unit environment. In this way, the functionality of the monitor may be customized depending on the type of smart sensor that is connected to it.

In a second alternate embodiment, the smart sensor memory module 40 may be used as a means of upgrading that portion of the monitor software that calculates the diagnostic index. In this embodiment, not only may different coefficients of the various variables in the diagnostic index be optimized for different applications, but the mathematical structure of the diagnostic index itself may be varied; ie., the variables in the index, their coefficients, and how they are combined may all be specified. This embodiment will greatly expand the flexibility of the smart sensor system by removing restrictions on the mathematical structure of the diagnostic index.

In a third alternate embodiment, the entire monitor software may be stored in the smart sensor memory module. In this embodiment, the monitor software may consist of only sufficient software to transfer the contents of the smart sensor memory module to the monitor 840 and then to run that software. Such software will include that portion which calculates the diagnostic index, as well as the portions that handle data acquisition, data display, communication with the user, etc.

All three of these alternate embodiments will allow new versions of diagnostic indices to be distributed as part of the smart sensor, rather than as an independent monitor software upgrade. This will simplify the task of upgrading the monitor software, as well as decreasing the associated cost. It will also ensure that each user of the smart sensor system has the latest monitor software available. While the memory capacity requirements for the third alternate embodiment cannot be satisfied by existing smart card memory modules, it is anticipated that the memory capacity of such devices will expand rapidly in the years ahead.

While the foregoing invention has been described with reference to its preferred embodiments, various alterations and modifications will occur to those skilled in the art. All such alterations and modifications are intended to fall within the scope of the appended claims.

We claim:

1. A smart sensor for acquiring electrophysiological signals comprising:
   an electrode array of at least two electrodes;
   a smart card semiconductor memory module for storing information,
   an interface platform connected to said electrode array, said interface platform carrying said smart card semiconductor memory module.

2. The smart sensor of claim 1 further comprising a substrate on which said electrode array is mounted.

3. The smart sensor of claim 2 further comprising at least one conductor connected to each of said at least two electrodes and terminating at a terminal tab.

4. The smart sensor of claim 3 wherein said interface platform includes mounting points for the memory module and terminal tab.

5. The smart sensor of claim 4 further comprising a mating receptacle which electrically connects said interface platform to a monitor containing a processor.

6. The smart sensor of claim 5, wherein said interface platform further comprises rails that properly align said interface platform in said mating receptacle.

7. The smart sensor of claim 5, wherein said mating receptacle further comprises a living hinged door that excludes liquids and contaminates.

8. The smart sensor of claim 5 wherein said mating receptacle comprises wiping surfaces which clean surfaces of said interface platform of liquids and contaminates.

9. The smart sensor of claim 5 wherein said mating receptacle further comprises a soft cover made of thermoplastic elastomer to maximize patient comfort.

10. The smart sensor of claim 5, where said mounting points hold said substrate and said memory module in an orientation such that contact pads of said memory module and conductors of said terminal tab are aligned in the same plane and placed adjacent each other so that said memory module passes into said mating receptacle before the said terminal tab conductors, preventing said terminal tab conductors from contacting the power supply lines of said memory module.

11. The smart sensor of claim 3 wherein an exposed conductor is interposed as a guard path between said electrode-connected conductors on the terminal tab and the conductive contacts of said memory module.

12. The smart sensor of claim 1 wherein said information is stored as a data string in said memory module, said data string including a lot code, sensor serial number and shelf life code.

13. The smart sensor of claim 1 wherein said information is stored as a data string in said memory module, said data string including an OEM code identifying the distributor of said smart sensor.

14. The smart sensor of claim 1 wherein said information is stored as a data string in said memory module, said data string including a usage counter indicating the number of uses remaining.

15. The smart sensor of claim 1 in which said information stored in said memory module includes coefficients used to calculate a diagnostic index.

16. The smart sensor of claim 1 in which said information stored in said memory module includes variables used to calculate a diagnostic index.

17. The smart sensor of claim 1 in which said information stored in said memory module includes a model structure used to calculate a diagnostic index.

18. The smart sensor of claim 1 in which said information stored in said memory module includes software for controlling a monitor to which the smart sensor is designed to be connected.

19. The smart sensor of claim 1 in which said information is encrypted using a security key algorithm.

20. The smart sensor of claim 19 in which various security keys are used for encryption/decryption, said keys in use being identified by a key code stored in said smart sensor memory module.

21. The smart sensor of claim 1 in which a digital signature is stored in said memory module, said digital signature being generated using a security key algorithm.

22. The smart sensor of claim 21 in which multiple security keys are used for generation of said digital signature, said keys in use being identified by a key code stored in said smart sensor memory module.

23. A smart sensor for acquiring electrophysiological signals comprising:
an electrode array of at least two electrodes;
a smart card semiconductor memory module for storing information, said memory device being mounted on one of said electrodes.

24. A smart sensor for acquiring electrophysiological signals comprising:
an electrode array of at least two electrodes;
a smart card semiconductor memory module for storing information,
a substrate for carrying said electrode array and said smart card semiconductor memory module.

25. A smart electrode for acquiring electrophysiological signals comprising:
a single electrode;
a smart card semiconductor memory module for storing information,
an interface platform for carrying said electrode and said smart card semiconductor memory device.

26. A smart electrode for acquiring electrophysiological signals comprising:
a single electrode;
a smart card semiconductor memory module for storing information,
an interface platform for carrying said smart card semiconductor memory device, and
a substrate connected to said interface platform and carrying said electrode.

27. A smart electrode for acquiring electrophysiological signals comprising:
a single electrode;
a smart card semiconductor memory module for storing information,
a substrate for carrying said electrode and said smart card semiconductor memory device.

28. A smart electrode for acquiring electrophysiological signals comprising:
a single electrode;
a smart card semiconductor memory module for storing information, said memory device being mounted on said electrode.

29. A smart sensor system comprising:
at least one smart electrode for acquiring electrophysiological signals including a single electrode, a smart card semiconductor memory module for storing information and a carrier for carrying said electrode and said smart card semiconductor memory module; and
a monitor containing a processor which runs authentication software for authenticating said at least one smart electrode, said monitor being connected to said carrier by a mating receptacle.

30. A smart sensor system of claim 29 wherein said carrier is an interface platform.

31. A smart sensor system of claim 29 wherein said carrier is a substrate.

32. The smart sensor system of claim 29 wherein said authentication software validates a digital signature stored in said memory module, wherein successful validation of said digital signature is required before said smart sensor is used for the acquisition of electrophysiological signals.

33. The smart sensor system of claim 32 in which multiple security keys are alternately used for digital signature validation, said keys being differentiated by a key code stored in said smart sensor memory module.

34. The smart sensor system of claim 29 in which said monitor further comprises a usage counter which is the mirror-image of a smart sensor memory module usage counter, said smart sensor memory module usage counter and said monitor usage counter being synchronized to a common value by said monitor.

35. The smart sensor system of claim 34 in which the common value is the lower of the uses remaining among said monitor usage counter and said sensor memory module usage counter.

36. The smart sensor system of claim 34 wherein said monitor uses said monitor usage counter to warn of smart sensor reuse.

37. The smart sensor system of claim 34 wherein said monitor uses said monitor usage counter to prevent the acquisition of electrophysiological signals from said smart sensor after more than a predefined number of reuses.

38. The smart sensor system of claim 29 wherein said monitor determines the smart sensor expiration date by adding the smart sensor's shelf life as determined from a shelf life code to its manufacturing date as determined from a lot code, said monitor comparing said expiration date to the current date to generate a user warning or prevent the acquisition of electrophysiological signals from said smart sensor if said expiration date is later than said current date.

39. The smart sensor of claim 29 wherein said information is stored as a data string in said memory module, said data string including the smart sensor expiration date.

40. The smart sensor system of claim 29 wherein said monitor compares a smart sensor expiration date to a current date to generate a user warning or prevent the acquisition of electrophysiological signals from said smart sensor if said expiration date is later than said current date.

41. The smart sensor system of claim 29 wherein said monitor uses the value of an OEM code to allow or disallow the acquisition of electrophysiological signals from said smart sensor.

42. The smart sensor system of claim 29 further comprising a ground fault detector, said detector comprising a current measuring circuit for monitoring the current through at least one patient conductor, said current being compared to a threshold value to detect a fault condition.

43. The smart sensor system of claim 42 where upon detection of said fault condition, said system first shuts down power to said memory module and, if said fault condition is not corrected, said system further shuts down power to the instrumentation amplifiers of said smart sensor system.

44. The smart sensor system of claim 43 where upon detection of said fault condition, said system alerts said monitor that a shutdown has occurred.

45. The smart sensor system of claim 29 wherein a guard path surrounds the patient conductors connected to said at least two electrodes said guard path being connected to the system ground within a mating receptacle and is designed to receive current in the event of a ground fault.

46. The smart sensor system of claim 29 further comprising a current detector, said current detector sensing the presence of sufficient current to operate said memory module to thereby determine whether said smart sensor is connected to a mating receptacle.

47. The smart sensor system of claim 46 wherein upon the detection of the connection of a smart sensor by said current detector, said current detector notifies said monitor which initiates authentication of said connected smart sensor.

48. The smart sensor system of claim 47 wherein after authentication of said smart sensor, said monitor initiates the configuration of said connected smart sensor system for operation appropriate to said detected smart sensor.

49. An interface to a smart sensor for acquiring electrophysiological signals comprising:

a monitor;

a smart card semiconductor memory module;

at least two electrodes;

at least four conductors, where at least two conductors of said at least four conductors connect said monitor to each of at least two electrodes, and at least two additional conductors of said at least four conductors connect said monitor to said smart card semiconductor memory module.

50. The smart sensor interface of claim 49 further comprising a ground fault detector, said detector including a current measuring circuit for monitoring current through at least one electrode-connected conductor, said current being compared to a threshold value to detect a fault condition.

51. The smart sensor interface of claim 49 further comprising a current detector, said current detector sensing in at least one of said conductors connected to the smart card memory module the presence of sufficient current to operate said memory module, the presence of said current thereby determining whether said smart sensor is connected to said interface.

52. The smart sensor interface of claim 49 further comprising a current detector, said current detector sensing the presence of current in a conductor loop, the ends of said conductor loop are connected to an interface voltage supply and ground, the presence of said current thereby determining whether said smart sensor is connected to said interface.

53. An interface to a smart electrode for acquiring electrophysiological signals comprising:

a monitor;

a smart card semiconductor memory module;

at least three conductors, where at least one conductor of said at least three conductors connects said monitor to a single electrode, and at least two additional conductors of said at least three conductors connect said monitor to said smart card semiconductor memory module.

* * * * *